(12) United States Patent
Huang

(10) Patent No.: US 8,222,287 B2
(45) Date of Patent: Jul. 17, 2012

(54) SUBSTITUTED ANTHRA[1,2-D]IMIDAZOLEDIONES AND PHARMACEUTICAL UTILITY THEREOF

(75) Inventor: Hsu-Shan Huang, Taipei (TW)

(73) Assignee: National Defense Medical Center, Taipei (TW)

(*) Notice: Subject to any disclaimer, the term of this patent is extended or adjusted under 35 U.S.C. 154(b) by 0 days.

(21) Appl. No.: 12/749,253

(22) Filed: Mar. 29, 2010

(65) Prior Publication Data

US 2010/0249143 A1    Sep. 30, 2010

Related U.S. Application Data

(62) Division of application No. 12/193,564, filed on Aug. 18, 2008, now abandoned.

(30) Foreign Application Priority Data

Apr. 2, 2008    (TW) ............................... 97112087 A

(51) Int. Cl.
*A61K 31/415*    (2006.01)
(52) U.S. Cl. ..................................... 514/393; 548/300.4
(58) Field of Classification Search .................. 514/393; 548/300.4
See application file for complete search history.

(56) References Cited

FOREIGN PATENT DOCUMENTS

| CA | 2428206 | | 9/2005 |
|---|---|---|---|
| SU | 499260 | * | 1/1976 |
| SU | 956516 | * | 9/1982 |

OTHER PUBLICATIONS

Chang, et al. J. Heterocycl. Chem., 33(2), 1996, 367-371.*
Maktit, et al. Journal Marocain de Chimie Heterocyclique, 6(1), 2007, 59-63.*
Chaudhuru, et al. Journal of Medicinal Chemistry, 50(10), 2007, 2536-2540.*
Gorelik, et al. Zhurnal Organicheskoi Khimii, 12(1), 1976, 177-186.*
Peng et al., "Colorimetric and Ratiometric Fluorescence Sensing of Fluoride: Tuning Selectivity in Proton Transfer" J. Org. Chem. 2005., vol. 70, No. 25, pp. 10524-10531.

Urquidi et al., "Role of Telomerase in Cell Senescence and Oncogenesis" Ann. Rev. Med., 2000, 51:65-79.
Bestilny et al., "Selective Inhibition of Telomerase Activity During Terminal Differentiation of Immortal Cell Lines" Cancer Research, Aug. 15, 1996, 56:3796-802.
Bodnar et al., "Extension of Life-Span by Introduction of Telomerase Into Normal Human Cells" Science, Jan. 16, 1998, 279:349-52.
Smogorzewska et al., "Regulation of Teomerase by Telomeric Proteins," Ann. Rev. Biochem., 2004, 73:177-208.
Klimasenko, et al., "X-Ray Diffraction Investigation of Anthraquinonediazoles III.* Crystal and Molecular Structure of Anthraquinonethiadiazole," Journal of Structural Chemistry (Zhurnal Stukturnoi Khimii), 14(1), 1973, 108-115.

* cited by examiner

*Primary Examiner* — James O Wilson
*Assistant Examiner* — Douglas M Willis
(74) *Attorney, Agent, or Firm* — Volpe and Koenig, P.C.

(57) ABSTRACT

A heteroannelated anthraquinone derivative compound is provided. The heteroannelated anthraquinone derivative compound is represented by a formula (I):

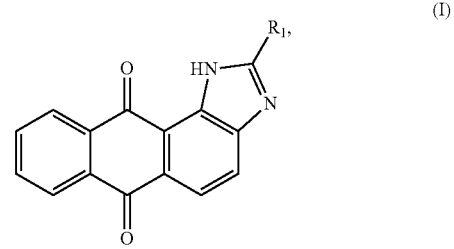

wherein $R_1$ is a substituent being one selected from a group consisting of i) a first substituent being one selected from a group consisting of a hydryl group, an amino group, a nitro group, a hydroxyl group and a cyan group, ii) a second substituent being one selected from a group consisting of $(CH_2)_n$ X, a straight $(CH_2)_n$ alkyl group, a $(CH_2)_n$ alkoxyl group, a branched $(CH_2)_n$ alkyl group, a $C_3$~$C_{12}$ nephthenic group, and a $C_3$~$C_{12}$ cyclic alkoxyl group, wherein $1 \leq n \leq 12$, and X is a halogen, iii) a third substituent being one selected from a group consisting of a straight $C_1$~$C_8$ alkyl group with a double-bond, a $C_1$~$C_8$ alkoxyl group with a double-bond, a branched $C_1$~$C_8$ alkyl group with a double-bond and a $C_3$~$C_8$ nephthenic group with a double-bond, and iv) a fourth substituent of a $C_5$~$C_{12}$ heterocyclic group.

12 Claims, No Drawings

SUBSTITUTED ANTHRA[1,2-D]IMIDAZOLEDIONES AND PHARMACEUTICAL UTILITY THEREOF

CROSS-REFERENCES TO RELATED APPLICATIONS

This is a divisional application of U.S. patent application Ser. No. 12/193,564 filed on Aug. 18, 2008 which is incorporated herein by reference as if fully set forth.

FIELD OF THE INVENTION

The present invention relates to heteroannelated anthraquinone derivatives for inhibiting a proliferation activity of a cancer cell, and more particularly to a series of heteroannelated anthraquinone derivatives and the synthesis method thereof.

BACKGROUND OF THE INVENTION

In normal somatic cells, the telomere, which is located at the end of a chromosome, gets shortened at each time of cell mitosis. When the telomere is shortened to some level, the cell will lose the ability of replication and go into apoptosis stage. Telomerase, which is a ribonucleoprotein, acts on the telomere in a eukaryocyte, so as to prolong or maintain the length of the telomere. A telomerase mainly includes two portions; one is a protein sub-unit with activity of reverse transcription, i.e. the human telomerase reverse transcriptase (hTERT), and the other one is an RNA template for synthesizing repeated sequences of the telomerase, i.e. the human telomerase RNA component (hTR), wherein the RNA template includes the single RNA sequence, -AAUCCC, which is complementary to the telomerase sequence. Telomerase activity is rarely detected in normal human somatic cells, but is usually detected in the cells that keep proliferating, such as hematopoietic cells, embryogenic cells, stem cells, etc. It is estimated that about 85-90% of human tumor cells have telomerase activity, and that is the reason why tumor cells do not go into apoptosis like a normal cell and can keep proliferating (Urquidi et al., *Annu. Rev. Med.* 2000, 51, 65-79). Reductions in hTERT mRNA expression level and telomerase activity are observed during the processes of cell going aged or immortalized (Bestilny et al., *Cancer Res.* 1996, 56, 3796-802). Furthermore, the telomerase activity of a somatic cell that should not express the telomerase activity could be reproduced by introduction of the hTERT cDNA thereinto for a high level expression of telomerase activity (Bodnar et al., *Science.* 1998, 279, 349-52).

The telomere at chromosome ends of eukaryotic cells is guanine-rich. In normal physiological conditions, the single strand DNA of the telomere spontaneously forms a G-quadruplex structure. The G-quadruplex structure includes two portions, wherein one is a small loop composed of TTA, and the other one is a guanine-tetrad composed of four guanines formed by cyclic hydrogen bonds. In order to inhibit the differentiation of tumor cells, an alternative besides the direct inhibition to telomerase activity is to stabilize the G-quadruplex structure for inhibiting its reaction with the complementary single strand RNA (AAUCCC), so as to prevent the telomerase from extending the telomere. Chromosome replications of tumor cells may be inhibited by the mentioned method, so as to achieve the anti-cancer effect directly or indirectly (Smogorzewska et al., *Annu. Rev. Biochem.* 2004, 73, 177-208).

It is observed in current studies that anthraquinone can stabilize the G-quadruplex structure for its formula with plane tri-cyclic structure. According to the researches to the quindoline derivatives (10H-indolo[3,2-b]quinoline) with tetra-cyclic structure, berberin with non-plane polycyclic structure and the analogs synthesized therefrom, it is known that the aromatic groups of the mentioned compounds play an important role in the bonding to the G-quadruplex structure. Over-expressions of known oncogenes usually induce cancers and are associated with many cell proliferation disorders, such as chronic lymphocytic leukemia, esophagus cancer, myeloma, etc. In additions, those genes also participate in many pathological and physiological processes. Many experiments have proved that over-expressions of tumor suppressor genes play important role in the prevention and treatment of tumors. Therefore, the research and development of the drugs for curing cell proliferation disorders can be applied in the cure of human cancers, just like the disclosures of Canadian Patent No. 2,428,206.

Although it has been published that a heteroannelated anthraquinone derivative can be synthesized by an acylation reaction of 1,2-diaminoanthraquinone to obtain a bis-substituent derivative, followed by a condensation reaction. However, this method only discloses the substituent of aromatic groups, and has a poor production rate (Peng et al., *J. Org. Chem.* 2005, 70, 10524-31).

Based on the above, the present invention provides heteroannelated anthraquinone derivatives and the synthesis method thereof, which is accomplished by preserving the chromophore group with plane tri-cyclic structure and the carbonyl groups at 9 and 10, which have better binding ability, then changing the tri-cyclic structure into tetra-cyclic structure and adding various side chains derived from different modified substituents, so as to synthesize a series of heteroannelated anthraquinone derivatives.

SUMMARY OF THE INVENTION

The present invention provides a series of heteroannelated anthraquinone derivatives for inhibiting the proliferation activity of cancer cells, which facilitate the study and application regarding cancer cells.

In accordance with the first aspect of the present invention, a heteroannelated anthraquinone derivative compound is provided. The compound is represented by a formula (I):

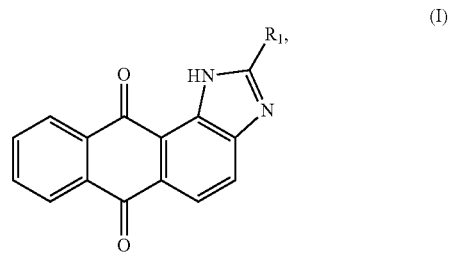

(I)

wherein $R_1$ is a substituent being one selected from a group consisting of i) a first substituent being one selected from a group consisting of a hydryl group, an amino group, a nitro group, a hydroxyl group and a cyan group, ii) a second substituent being one selected from a group consisting of $(CH_2)_n$ X, a straight $(CH_2)_n$ alkyl group, a $(CH_2)_n$ alkoxyl group, a branched $(CH_2)_n$ alkyl group, a $C_3$~$C_{12}$ nephthenic group, and a $C_3$~$C_{12}$ cyclic alkoxyl group, wherein $1 \leq n \leq 12$, and X is a halogen, iii) a third substituent being one selected from a group consisting of a straight $C_1$~$C_8$ alkyl group with a double-bond, a $C_1$~$C_8$ alkoxyl group with a double-bond, a branched $C_1$~$C_8$ alkyl group with a double-bond and a $C_3$~$C_8$ nephthenic group with a double-bond, and iv) a fourth substituent of a $C_5$~$C_{12}$ heterocyclic group, wherein one of the nephthenic group and the heterocyclic group further has at least one of an ortho-substitution, a meta-substitution and a para-substitution, and comprises at least a fifth substituent for any of the substitutions being one selected from a group consisting of an alkyl group with a $C_1$~$C_3$ substituent branch, an amino group, a nitro group, a hydroxyl group and a cyan group, a $C_1$~$C_5$ alkyl group, a halogen substituted $C_1$~$C_5$ alkyl group, a $C_1$~$C_5$ alkoxyl group, a halogen substituted $C_1$~$C_5$ alkoxyl group, a $C_1$~$C_5$ cyclic alkoxyl group, and a halogen substituted $C_1$~$C_5$ cyclic alkoxyl group.

Preferably, the halogen is one selected from a group consisting of a fluorine, a chlorine, a bromine and an iodine.

Preferably, the second substituent is one selected from a group consisting of a methyl group, an ethyl group, a propyl group, a butyl group, an isobutyl group, a pentyl group, an isopentyl group, a cyclopentyl group, a heptyl group, an isoheptyl group, a cycloheptyl group, an octyl group, an isooctyl group, a cyclooctyl group, a straight alkyl group with a branch substituted by a straight $C_1$~$C_5$ alkyl group, a nephthenic group with a branch substituted by a straight $C_1$~$C_5$ alkyl group, alkoxyl derivatives of the mentioned alkyl groups, and halogenated derivatives of the mentioned alkyl groups.

Preferably, the third substituent is one selected from a group consisting of a vinyl group, a propenyl group, a butenyl group, an isobutenyl group, a pentenyl group, an isopentenyl group, a cyclopentenyl group, a hexenyl group, a cyclohexenyl group, a heptenyl group, an cycloheptenyl group, a straight alkyl group with a branch substituted by a straight $C_1$~$C_3$ alkyl group, a nephthenic group with a branch substituted by a straight $C_1$~$C_3$ alkyl group, alkoxyl derivatives of the mentioned groups, and halogenated derivatives of the mentioned groups.

Preferably, the heteroannelated anthraquinone derivative compound is used as an effective component together with an excipient to provide a pharmaceutic composition for inhibiting one selected from a group consisting of a growth of a cancer cell, a disease of cell proliferation, and a growth of cell telomere.

In accordance with the second aspect of the present invention, a heteroannelated anthraquinone derivative compound is provided. The compound is represented by a formula (II):

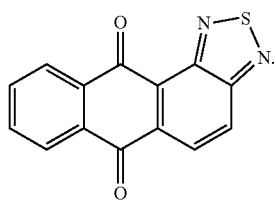

(II)

Preferably, the heteroannelated anthraquinone derivative compound is used as an effective component together with an excipient to provide a pharmaceutic composition for inhibiting one selected from a group consisting of a growth of a cancer cell, a disease of cell proliferation, and a growth of cell telomere.

In accordance with the third aspect of the present invention, a heteroannelated anthraquinone derivative compound is provided. The compound is represented by a formula (III):

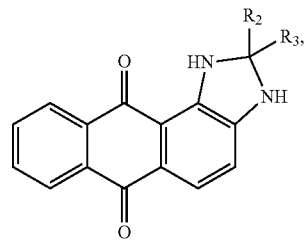

(III)

wherein either one of $R_2$ and $R_3$ is one of i) a first substituent being one of a hydryl group and a sulfuryl-group, and ii) a second substituent being one selected from a group consisting of a $C_1$~$C_8$ alkyl group, a $C_1$~$C_8$ alkoxyl group, a $C_3$~$C_8$ nephthenic group, and a $C_3$~$C_8$ cyclic alkoxyl group, a straight alkyl group with a branch substitutent, a nephthenic group with a branch substitutent by a straight $C_1$~$C_5$ alkyl group and halogenated derivatives of the mentioned substituent groups.

Preferably, the second substituent is one selected from a group consisting of a methyl group, an ethyl group, a propyl group, a butyl group, an isobutyl group, a pentyl group, an isopentyl group, a cyclopentyl group, a heptyl group, an isoheptyl group, a cycloheptyl group, an octyl group, an isooctyl group, a cyclooctyl group, a phenyl group, a benzyl group, a phenethyl group, a straight alkyl group with a branch substituted by a straight $C_1$~$C_3$ alkyl group, a nephthenic group with a branch substituted by a straight $C_1$~$C_3$ alkyl group, alkoxyl derivatives of the mentioned substituent groups, and halogenated derivatives of the mentioned substituent groups.

Preferably, the heteroannelated anthraquinone derivative is used as an effective component together with an excipient to provide a pharmaceutic composition for inhibiting one selected from a group consisting of a growth of a cancer cell, a disease of cell proliferation, and a growth of cell telomere.

In accordance with the fourth aspect of the present invention, a heteroannelated anthraquinone derivative compound is provided. The compound is represented by a formula (IV):

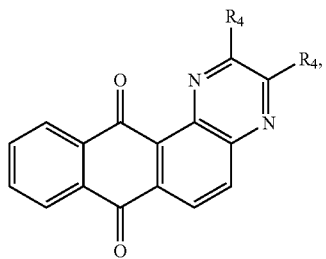

(IV)

wherein $R_4$ is one selected from a group consisting of a hydryl group, a $C_1$~$C_4$ alkyl group, a $C_1$~$C_4$ alkoxyl group, a $C_1$~$C_4$ ketone group, a straight alkyl group with a branch substituted by a straight $C_1$~$C_3$ alkyl group, a halogen substituted $C_1$~$C_4$ alkyl group, and a $C_1$~$C_4$ alkoxyl group.

Preferably, A compound as claimed in claim 12, being used as an effective component together with an excipient to provide a pharmaceutic composition for inhibiting one selected from a group consisting of a growth of a cancer cell, a disease of cell proliferation, and a growth of cell telomere.

In accordance with the fifth aspect of the present invention, a method for manufacturing a compound having the formula (I) is provided. The method includes steps of a) dissolving a diaminoanthraquinone in a dimethylformamide solution for forming a solution A, b) adding and dissolving a chloroacetyl chloride in the solution A for forming a solution B, c) mixing and reacting the solution B by a reverse flow method, and then transferring the solution B into an icy water for forming a solution C, d) filtering the solution C for obtaining a precipitate, and e) washing the precipitate by using an ethanol for obtaining the compound of the formula (I).

In accordance with the sixth aspect of the present invention, a method for manufacturing a compound having the formula (I) is provided. The method includes steps of a) dissolving a diaminoanthraquinone in a dimethylformamide solution for forming a solution A, b) adding and dissolving a reagent in the solution A for forming a solution B, wherein the reagent is one of a benzaldehyde and a carbon disulfide, c) catalyzing a reaction of the solution B by adding a concentrated sulfuric acid thereinto, and then transferring the solution B into an ice water for forming a solution C, d) filtering the solution C for obtaining a precipitate, and e) washing the precipitate by using an ethanol for obtaining the compound of the formula (I), wherein when the reagent is the carbon disulfide, a triethylamine is further added into the solution B before the step c).

In accordance with the seventh aspect of the present invention, a method for manufacturing a compound having the formula (III) is provided. The method includes steps of a) dissolving a diaminoanthraquinone in an acetone for forming a solution A, b) adding a concentrated sulfuric acid into the solution A for forming a solution B, c) transferring the solution B into a potassium carbonate column for obtaining a solution C, and d) using a methanol to crystallize the compound of the formula (III) in the solution C.

Preferably, the step b) is performed in a room temperature.

In accordance with the eighth aspect of the present invention, a method for manufacturing a compound having the formula (IV) is provided. The method includes steps of a) dissolving a diaminoanthraquinone in a dimethylformamide solution for forming a solution A, b) adding a glyoxal ethanol solution into the solution A for forming a solution B, c) reacting the solution B by a reverse flow reaction, d) filtering the solution B for obtaining a precipitate, and e) washing the precipitate by using a hot alcohol and a dichloromethane for separating out the compound of the formula (IV).

Alternatively, in some steps of the above-mentioned methods, the production rate will increase if the solvents used for dissolving the diaminoanthraquinone contain less water. In the purification steps for the products, alcohol could be used for crystallization; alternatively, hot alcohol could be used for washing the products. The products with high solubility could be dissolved in alcohol before crystallization. The products with low solubility need to be washed by hot alcohol to wash out initial material or impurities and by-products generated in the reaction. Compared with recrystallization, although parts of products would be lost in the washing steps, it would be easier to obtain the purified products.

The compound provided in the present invention could be supplied with excipients, carriers or diluent, such starch or binder like carboxymethyl cellulose (CMC), so as to prepare granulated pill, tablet, or capsule. Alternatively, the compound could be dissolved in phosphate buffer for adjusting the pH thereof, so as to prepare injection. The compound could be supplied with penetration enhancer, so as to prepare absorbate by skin.

Additional objects and advantages of the invention will be set forth in the following descriptions.

DETAILED DESCRIPTION OF THE PREFERRED EMBODIMENT

The present invention will now be described more specifically with the experiment results of the following embodiments. It is to be noted that the following descriptions of preferred embodiments of this invention are presented herein for the purposes of illustration and description only; it is not intended to be exhaustive or to be limited to the precise form disclosed.

Concretely speaking, the method for manufacturing the heteroannelated anthraquinone derivative includes cyclization and condensation reactions.

Embodiment 1 (2-Methyl-1(3)H-anthra[1,2-d]imidazole-6,11-dione, No. 2)

1,2-Diaminoanthraquinone (1.19 g, 5 mmol) is dissolved in 30 mL of N,N-dimethylformamide, and chloroacetyl chloride (0.5 mL, 6 mmol) is added thereinto. After ten hours of mixing and reacting by a reverse flow, the mixture is transferred into 200 mL of icy water. After filtering, the precipitate is collected and washed by hot alcohol, so as to obtain the black compound No. 2.

The compound No. 2 has the following characterstics: MW 262.0724 ($C_{16}H_9N_2O_2$); $R_f$: 0.79 (ethyl acetate:dichloromethane=1:4); IR (KBr) cm$^{-1}$: 1667 (CO); EI-MS m/z: 262 (M$^+$, 100%); $^1$H-NMR (300 MHz, DMSO-$d_6$) δ (ppm): 2.72 (3H, s, —CH$_3$), 7.75-7.82 (2H, m, Ar—H$_{7,10}$), 7.93 (1H, d, J=8.4 Hz, Ar—H$_5$), 8.13 (1H, d, J=8.4 Hz, Ar—H$_4$), 8.19-8.23 (1H, m, Ar—H$_{8,9}$), 11.01 (1H, br, —NH); and $^{13}$C-NMR (75 MHz, DMSO-$d_6$) δ (ppm): 23.89, 120.23, 121.22, 125.29, 126.19, 126.75, 127.19, 128.17, 128.87, 132.98, 134.18, 134.42, 148.22, 158.09, 182.43 (CO), 185.13 (CO).

Embodiment 2 (2-Chloroacetyl-1(3)H-anthra[1,2-d]imidazole-6,11-dione, No. 3)

Except controlling the reacting temperature in 50-60° C., all steps are identical with the steps for manufacturing the compound No. 2, and the yellowish brown compound No. 3 can be obtained.

The compound No. 3 has the following characterstics: MW 296.0353 ($C_{16}H_9N_2O_2Cl$); $R_f$: 0.5 (ethyl acetate:dichloromethane=1:4); IR (KBr) cm$^{-1}$: 3359 (NH), 1660 (CO); HRMS (ESI-TOF) m/z: calcd for $C_{16}H_{10}N_2O_2Cl^+$ [M+H]$^+$: 297.0425, found: 297.0426; $^1$H-NMR (300 MHz, CDCl$_3$) δ (ppm): 4.92 (2H, s, —CH$_2$Cl), 7.80-7.83 (2H, m, Ar—H$_{7,10}$), 8.08 (1H, d, J=8.4 Hz, Ar—H$_5$), 8.24 (1H, d, J=8.4 Hz, Ar—H$_4$), δ8.26-8.35 (2H, m, Ar—H$_{8,9}$), δ11.21 (1H, br, —NH); and $^{13}$C-NMR (75 MHz, DMSO) δ (ppm): 37.80, 119.35, 121.27, 125.95, 126.83, 127.40, 129.06, 132.35, 133.47, 133.64, 134.88, 135.10, 148.89, 156.93, 183.04 (CO), 183.83 (CO).

Embodiment 3 (2-Ethyl-1(3)H-anthra[1,2-d]imidazole-6,11-dione, No. 4)

1,2-Diaminoanthraquinone (1.19 g, 5 mmol) was dissolved in dimethylformamide (30 mL), and propionaldehyde (0.29 g, 5 mmol) is added thereinto. Concentrated sulfuric acid (0.1 mL) is added thereinto for catalyzation. After mixing and reacting at room temperature for one hour, the reacted mixture is transferred into 200 mL of icy water and is extracted by using dichloromethane. The extract is dried, and crystallized by using alcohol, so as to obtain the brown compound No. 4.

The compound No. 4 has the following characterstics: MW 276.0899 ($C_{17}H_{12}N_2O_2$); $R_f$: 0.75 (ethyl acetate:dichloromethane=1:4); IR (KBr) cm$^{-1}$: 1669 (CO); HRMS (ESI-TOF) m/z: calcd for $C_{17}H_{13}N_2O_2^+$ [M+H]$^+$: 277.0971, found: 277.0975 calcd for $C_{17}H_{12}N_2O_2Na^+$ [M+Na]$^+$: 299.0971, found: 299.0794; $^1$H-NMR (300 MHz, CDCl$_3$) δ

(ppm): 1.51 (3H, t, J=7.5 Hz, —CH$_3$), 3.05 (2H, q, J=7.5 Hz, —CH$_2$—), 7.73-7.81 (2H, m, Ar—H$_{7,10}$), 7.99 (1H, d, J=8.4 Hz, Ar—H$_5$), δ8.16 (1H, d, J=8.4 Hz, Ar—H$_4$), δ8.21-8.23 (1H, m, Ar—H$_9$), δ8.27-8.31 (1H, m, Ar—H$_8$), δ10.85 (1H, br, —NH); and $^{13}$C-NMR (75 MHz, CDCl$_3$) δ (ppm): 11.87, 22.89, 117.74, 121.50, 125.21, 126.47, 127.55, 128.21, 132.72, 133.24, 133.72, 133.99, 134.37, 148.90, 161.64, 182.81 (CO), 185.15 (CO).

Embodiment 4 (2-Isopropyl-1(3)H-anthra[1,2-d]imidazole-6,11-dione, No. 5)

All steps for manufacturing the yellow compound No. 5 are identical with the steps of Embodiment 3, except that propionaldehyde is substituted by isobutyraldehyde (0.41 g, 5 mmol).

The compound No. 5 has the following characterstics: MW 290.1055 (C$_{18}$H$_{14}$N$_2$O$_2$); R$_f$: 0.7 (ethyl acetate:dichloromethane=1:4); IR (KBr) cm$^{-1}$: 3445 (NH), 1662 (CO); HRMS (ESI-TOF) m/z: calcd for C$_{18}$H$_{15}$N$_2$O$_2$$^+$ [M+H]$^+$: 291.1120, found: 291.1123; $^1$H-NMR (300 MHz, CDCl$_3$) δ (ppm): δ1.56 (6H, d, J=6.6 Hz, —CH$_3$), δ3.40 (1H, sp, J=6.6 Hz, —CH—), δ7.78-7.85 (2H, m, Ar—H$_{7,10}$), δ8.11 (1H, d, J=8.4 Hz, Ar—H$_5$), δ8.23 (1H, d, J=8.4 Hz, Ar—H$_4$), δ8.25-8.36 (2H, m, Ar—H$_{8,9}$), δ10.88 (1H, s, —NH); and $^{13}$C-NMR (75 MHz, CDCl$_3$) δ (ppm): 21.15, 29.21, 117.66, 121.36, 125.21, 126.32, 127.42, 128.05, 132.49, 133.10, 133.61, 133.86, 134.24, 148.71, 165.35, 181.05 (CO), 182.73 (CO).

Embodiment 5 (2-Butyl-1(3)H-anthra[1,2-d]imidazole-6,11-dione, No. 6)

All steps for manufacturing the brown compound No. 6 are identical with the steps of Embodiment 3, except that propionaldehyde is substituted by pentanal (0.45 g, 5 mmol).

The compound No. 6 has the following characterstics: MW 304.1212 (C$_{19}$H$_{16}$N$_2$O$_2$); R$_f$: 0.65 (ethyl acetate:dichloromethane=1:4); IR (KBr) cm$^{-1}$: 1669 (CO); HRMS (ESI-TOF) m/z: calcd for C$_{19}$H$_{17}$N$_2$O$_2$$^+$ [M+H]$^+$: 305.1276, found: 305.1282 calcd for C$_{19}$H$_{15}$N$_2$O$_2$$^-$ [M−H]$^-$: 303.1131, found: 303.1135; $^1$H-NMR (300 MHz, CDCl$_3$) δ (ppm): δ1.00 (3H, t, J=7.2 Hz, —CH$_3$), δ1.50 (2H, sx, J=7.5 Hz, —CH$_2$—), δ1.93 (2H, qt, J=7.8 Hz, —CH$_2$—), δ3.04 (2H, t, J=7.5 Hz, —CH$_2$—), δ7.62-7.83 (2H, m, Ar—H$_{7,10}$), δ8.03 (1H, d, J=8.4 Hz, Ar—H$_5$), δ8.20 (1H, d, J=8.1 Hz, Ar—H$_4$), δ8.24-8.35 (2H, m, Ar—H$_{8,9}$), δ10.83 (1H, s, —NH); and $^{13}$C-NMR (75 MHz, CDCl$_3$) δ (ppm): 12.98, 21.78, 28.60, 29.27, 117.32, 121.07, 124.64, 125.98, 127.08, 127.83, 132.17, 132.84, 133.20, 133.61, 133.86, 148.25, 160.29, 182.31 (CO), 184.78 (CO).

Embodiment 6 (2-sec-Butyl-1(3)H-anthra[1,2-d]imidazole-6,11-dione, No. 7)

All steps for manufacturing the yellow compound No. 7 are identical with the steps of Embodiment 3, except that propionaldehyde is substituted by methylbutyraldehyde (0.46 g, 5 mmol).

The compound No. 7 has the following characterstics: MW 304.1212 (C$_{19}$H$_{16}$N$_2$O$_2$); R$_f$: 0.57 (ethyl acetate:dichloromethane=1:4); IR (KBr) cm$^{-1}$: 1665 (CO); HRMS (ESI-TOF) m/z: calcd for C$_{19}$H$_{15}$H$_{17}$N$_2$O$_2$$^+$ [M+H]$^+$: 305.1276, found: 305.1280 calcd for C$_{19}$H$_{15}$N$_2$O$_2$$^-$ [M−H]$^-$: 303.1131, found: 303.1137; $^1$H-NMR (300 MHz, CDCl$_3$) δ (ppm): δ1.00 (3H, t, J=7.2 Hz, —CH$_3$), δ1.52 (3H, d, J=6.9 Hz, —CH$_3$), δ1.82-2.02 (2H, m, —CH$_2$—), δ3.04 (1H, sx, J=7.2 Hz, —CH—), δ7.62-7.83 (2H, m, Ar—H$_{7,10}$), δ8.03 (1H, d, J=8.4 Hz, Ar—H$_5$), δ8.20 (1H, d, J=8.1 Hz, Ar—H$_4$), δ8.24-8.35 (2H, m, Ar—H$_{8,9}$), δ10.83 (1H, s, —NH); and $^{13}$C-NMR (75 MHz, CDCl$_3$) δ (ppm): 11.09, 18.09, 28.40, 35.71, 117.39, 121.07, 124.75, 125.95, 127.09, 127.84, 131.92, 132.83, 133.22, 133.59, 133.87, 148.06, 164.30, 182.31 (CO), 184.82 (CO).

Embodiment 7 (2-tert-Butyl-1(3)H-anthra[1,2-d]imidazole-6,11-dione, No. 8)

All steps for manufacturing the yellow compound No. 8 are identical with the steps of Embodiment 3, except that propionaldehyde is substituted by trimethylacetaldehyde (0.46 g, 5 mmol).

The compound No. 8 has the following characterstics: MW 304.1212 (C$_{19}$H$_{16}$N$_2$O$_2$); R$_f$: 0.8 (ethyl acetate:dichloromethane=1:4); IR (KBr) cm$^{-1}$: 3568 (NH), 1664 (CO); HRMS (ESI-TOF) m/z: calcd for C$_{19}$H$_{17}$N$_2$O$_2$$^+$ [M+H]$^+$: 305.1276, found: 305.1283 calcd for C$_{19}$H$_{15}$N$_2$O$_2$$^-$ [M−H]$^-$: 303.1131, found: 303.1136; $^1$H-NMR (300 MHz, CDCl$_3$) δ (ppm): δ1.58 (9H, s, —C(CH$_3$)$_3$), δ7.77-7.84 (2H, m, Ar—H$_{7,10}$), δ8.08 (1H, d, J=8.4 Hz, Ar—H$_5$), δ8.21 (1H, d, J=8.4 Hz, Ar—H$_4$), δ8.25-8.28 (1H, m, Ar—H$_8$), δ8.33-8.36 (1H, m, Ar—H$_9$), δ10.83 (1H, s, —NH); and $^{13}$C-NMR (75 MHz, CDCl$_3$) δ (ppm): 29.24, 117.79, 121.47, 125.41, 126.39, 127.56, 128.17, 132.70, 133.23, 133.74, 133.96, 134.37, 148.73, 168.00, 182.77 (CO), 185.26 (CO).

Embodiment 8 (2-Heptyl-1(3)H-anthra[1,2-d]imidazole-6,11-dione, No. 9)

All steps for manufacturing the brown compound No. 9 are identical with the steps of Embodiment 3, except that propionaldehyde is substituted by octanal (0.29 g, 5 mmol).

The compound No. 9 has the following characterstics: MW 346.1681 (C$_{22}$H$_{22}$N$_2$O$_2$); R$_f$: 0.85 (ethyl acetate:dichloromethane=1:4); IR IR (KBr) cm$^-$: 3447 (NH), 1664 (CO); HRMS (ESI-TOF) m/z: calcd for C$_{22}$H$_{23}$N$_2$O$_2$$^+$ [M+H]$^+$: 347.1754, found: 347.1752; $^1$H-NMR (300 MHz, CDCl$_3$) δ (ppm): δ0.87-0.91 (3H, m, —CH$_3$), δ1.26-1.35 (6H, m, —CH$_2$—), δ1.56 (2H, sx, J=7.0 Hz, —CH$_2$—), δ2.36 (2H, q, J=7.0 Hz, —CH$_2$—), δ2.71 (2H, t, J=7.0 Hz, —CH$_2$—), δ7.75-7.81 (2H, m, Ar—H$_{7,10}$), δ8.04 (1H, d, J=8.0 Hz, Ar—H$_5$), δ8.17 (1H, d, J=8.0 Hz, Ar—H$_4$), δ8.23-8.25 (1H, m, Ar—H$_8$), δ8.31-8.33 (1H, m, Ar—H$_9$), δ10.93 (1H, s, —NH); and $^{13}$C-NMR (75 MHz, CDCl$_3$) δ (ppm): 14.08, 22.63, 27.99, 28.79, 29.24, 29.46, 31.79, 117.49, 121.66, 125.28, 126.37, 127.54, 130.56, 133.27, 133.67, 134.06, 134.31, 137.37, 149.40, 158.89, 182.69 (CO), 185.25 (CO).

Embodiment 9 ((E)-2-(But-1-enyl)-1(3)H-anthra[1,2-d]imidazole-6,11-dione, No. 10)

All steps for manufacturing the brown compound No. 10 are identical with the steps of Embodiment 3, except that propionaldehyde is substituted by trans-2-pentenal (0.46 g, 5 mmol).

The compound No. 10 has the following characterstics: MW 302.1055 (C$_{19}$H$_{15}$N$_2$O$_2$); R$_f$: 0.57 (ethyl acetate:dichloromethane=1:4); IR (KBr) cm$^{-1}$: 1664 (CO); EI-MS m/z: 302 (M$^+$, 100%); $^1$H-NMR (300 MHz, CDCl$_3$) δ (ppm): δ0.98 (3H, t, J=6.9 Hz, —CH$_3$), δ1.94-1.98 (2H, m, —CH$_2$—), δ6.16-6.29 (1H, m, —CH—), δ6.51 (1H, d, J=18 Hz, —CH—), δ7.68 (1H, d, J=8.4 Hz, Ar—H$_5$), δ7.82-7.89 (2H, m, Ar—H$_{7,10}$), δ8.14 (1H, d, J=8.1 Hz, Ar—H$_4$), δ8.27-8.35 (2H, m, Ar—H$_{8,9}$), δ10.74 (1H, s, —NH); and $^{13}$C-NMR (75 MHz, CDCl$_3$) δ (ppm): 14.39, 27.40, 117.37, 120.03, 121.07, 124.75, 125.95, 127.09, 127.84, 131.92, 132.83, 133.22, 133.59, 133.87, 134.90, 135.37, 149.06, 182.73 (CO), 185.18 (CO).

Embodiment 10 (2-Mercapto-1(3)H-anthra[1,2-d]imidazole-6,11-dione, No. 23)

1,2-Diaminoanthraquinone (1.19 g, 5 mmol) is dissolved in N,N-dimethylformamide (30 mL), and triethylamine (3 mL) is further added thereinto after carbon disulfide (0.4 g, 5 mmol) is added thereinto. After mixing in room temperature and performing reverse flow for ten hours, the reacted mixture is transferred into 200 mL of icy water. After filtering, the precipitate is collected and washed by hot alcohol, so as to obtain reddle compound No. 23 with melting point of 407-409° C., and the production rate is 80%.

The compound No. 23 has the following characterstics: MW 280.0306 ($C_{15}H_8N_2O_2S$); $R_f$: 0.80 (ethyl acetate:dichloromethane=1:4); IR (KBr) cm$^{-1}$: 3221 (NH), 3192 (NH), 1665 (CO); HRMS (ESI-TOF) m/z: calcd for $C_{15}H_9N_2O_2S^+$ [M+H]$^+$: 281.0379, found: 281.0389; $^1$H-NMR (300 MHz, DMSO-$d_6$) δ (ppm): δ7.54 (1H, d, J=8.1 Hz, Ar—$H_5$), δ8.02 (1H, d, J=8.1 Hz, Ar—$H_4$), δ7.91-7.94 (2H, m, Ar—$H_{7,10}$), δ8.18-8.22 (2H, m, Ar—$H_{8,9}$), δ12.73 (1H, s, —NH), δ13.29 (1H, s, —NH); and $^{13}$C-NMR (75 MHz, DMSO-$d_6$) δ (ppm): 113.89, 115.27, 122.41, 126.26, 126.76, 126.88, 130.95, 132.89, 133.06, 134.25, 134.47, 138.19, 172.89, 181.79 (CO), 182.46 (CO).

Embodiment 11 (2-Phenyl-1(3)H-anthra[1,2-d]imidazole-6,11-dione, No. 11)

1,2-Diaminoanthraquinone (1.19 g, 5 mmol) is dissolved in dimethylformamide (30 mL), and concentrated sulfuric acid (0.1 mL) is further added thereinto for catalyzation after benzaldehyde (0.6 mL, 5 mmol) is added thereinto. After mixing and reacting in room temperature for one hour, the reacted mixture is transferred into 200 mL of icy water. After filtering, the precipitate is collected and washed by hot alcohol, so as to obtain yellowish brown compound No. 11.

The compound No. 11 has the following characterstics: MW 324.0899 ($C_{21}H_{12}N_2O_2$); $R_f$: 0.55 (ethyl acetate:dichloromethane=1:4); IR (KBr) cm$^{-1}$: 3296 (NH), 1660 (CO); EI-MS m/z: 324 (M$^+$, 100.00%), 325 (19%); HRMS (ESI-TOF) m/z: calcd for $C_{21}H_{13}N_2O_2^+$ [M+H]$^+$: 325.0971, found: 325.0973; $^1$H-NMR (300 MHz, DMSO-$d_6$) δ (ppm): δ7.57 (3H, t, J=3 Hz, Ar'—$H_{3,4,5}$), δ7.89 (2H, m, Ar—$H_{7,10}$), δ8.03 (1H, d, J=8.4 Hz, Ar—$H_5$), δ8.08 (1H, d, J=8.4 Hz, Ar—$H_4$), δ8.16 (2H, m, Ar—$H_{8,9}$), δ8.40 (2H, dd, J=6, 3 Hz, Ar'—$H_{2,6}$); and $^{13}$C-NMR (75 MHz, DMSO-$d_6$) δ (ppm): 119.62, 121.72, 125.06, 126.85, 127.42, 128.79, 128.86, 129.41, 129.50, 131.72, 133.72, 133.77, 134.92, 135.07, 149.26, 158.25, 183.06 (CO), 183.79 (CO).

Embodiment 12 (2-(4-N,N-Dimethylamino)phenyl-1(3)H-anthra[1,2-d]imidazole-6,11-dione, No. 12)

All steps for manufacturing the deep brown compound No. 12 are identical with the steps of Embodiment 11, except that benzaldehyde is substituted by 4-dimethylaminobenzaldehyde (0.77 g, 5 mmol).

The compound No. 12 has the following characterstics: MW 367.1321 ($C_{23}H_{17}N_3O_2$); $R_f$: 0.6 (ethyl acetate:dichloromethane=1:4); IR (KBr) cm$^{-1}$: 3404 (NH), 1659 (CO); EI-MS m/z: 366 (27%), 367 (M$^+$, 100.00%), 368 (20%); HRMS (ESI-TOF) m/z: calcd for $C_{23}H_{18}N_3O_2^+$ [M+H]$^+$: 368.1393, found: 368.1393; $^1$H-NMR (300 MHz, CDCl$_3$) δ (ppm): δ3.09 (6H, s, —N(CH$_3$)$_2$), δ6.81 (2H, d, Ar—H), δ7.79~7.82 (3H, m, Ar—H), δ8.03-8.22 (3H, m, Ar—H), δ8.27~8.36 (2H, m, Ar—H), δ11.10 (1H, br, —NH); and $^{13}$C-NMR (75 MHz, CDCl$_3$) δ (ppm): 39.95, 111.65, 115.23, 117.13, 121.83, 124.24, 126.33, 127.37, 127.44, 128.27, 133.27, 133.45, 133.54, 134.12, 150.11, 152.10, 157.59, 182.47 (CO), 185.09 (CO).

Embodiment 13 (2-(4-Nitrophenyl)-1(3)H-anthra[1,2-d]imidazole-6,11-dione, No. 13)

All steps for manufacturing the deep brown compound No. 13 are identical with the steps of Embodiment 11, except that benzaldehyde is substituted by 4-nitrobenzaldehyde (0.78 g, 5 mmol).

The compound No. 13 has the following characterstics: MW 369.0750 ($C_{21}H_{11}N_3O_4$); $R_f$: 0.6 (ethyl acetate:dichloromethane=1:4); IR (KBr) cm$^{-1}$: 3460 (NH), 1657 (CO), 1517, 1345 (NO$_2$); EI-MS m/z: 249 (100%), 369 (M$^+$, 35%); HRMS (ESI-TOF) m/z: calcd for $C_{21}H_{12}N_3O_4^+$ [M+H]$^+$: 370.0822, found: 370.0823; $^1$H-NMR (300 MHz, DMSO-$d_6$) δ (ppm): δ7.79-7.82 (3H, m, Ar—$H_{7,10}$), δ7.14 (1H, d, J=8.1 Hz, Ar—$H_4$), δ8.23 (1H, d, J=8.1 Hz, Ar—$H_5$), δ8.23-8.32 (2H, m, Ar—$H_{8,9}$), δ8.39 (2H, d, J=8.1 Hz, Ar'—$H_{2,6}$), δ8.58 (2H, d, J=8.1 Hz, Ar'—$H_{3,5}$), δ10.15 (1H, br, —NH); and $^{13}$C-NMR (75 MHz, DMSO-$d_6$) δ (ppm): 117.81, 122.43, 123.62, 125.24, 125.88, 126.10, 127.92, 133.22, 133.36, 134.53, 143.08, 146.39, 146.77, 155.89, 172.18, 178.35, 179.40, 183.20 (CO), 185.56 (CO).

Embodiment 14 (2-(4-Hydroxy-3-methoxyphenyl)-1H-anthra[1,2-d]imidazole-6,11-dione, No. 14)

1,2-Diaminoanthraquinone (1.19 g, 5 mmol) is dissolved in dimethylformamide (30 mL), and concentrated sulfuric acid (0.1 mL) is further added thereinto for catalyzation after vanillin (0.77 g, 5 mmol) is added thereinto. After mixing and reacting in room temperature for one hour, the reacted mixture is transferred into 200 mL of icy water. After filtering, the precipitate is collected and washed by hot alcohol, so as to obtain brown compound No. 14.

The compound No. 14 has the following characterstics: MW 370.0954 ($C_{22}H_{14}N_2O_4$); $R_f$: 0.2 (ethyl acetate:dichloromethane=1:4); IR (KBr) cm$^{-1}$: 3411 (OH), 3411 (NH), 1664 (CO); EI-MS m/z: 369 (57%), 370 (M$^+$, 100%) HRMS (ESI-TOF) m/z: calcd for $C_{22}H_{15}N_2O_4^+$ [M+H]$^+$: 370.1026, found: 370.1025; $^1$H-NMR (300 MHz, DMSO-$d_6$) δ (ppm): δ3.91 (3H, s, —OCH$_3$), δ6.90 (1H, d, J=8.4 Hz, Ar'—$H_5$), δ7.81-7.88 (3H, m, Ar—$H_{7,10}$, Ar'—$H_2$), δ7.92-7.96 (3H, m, Ar—$H_{4,5}$, Ar'—$H_6$), δ7.99 (1H, s, —NH), δ8.11 (2H, td, J=Hz, Ar—$H_{8,9}$), δ9.78 (1H, br, —OH); and $^{13}$C-NMR (75 MHz, DMSO-$d_6$) δ (ppm): 56.57, 112.72, 116.37, 119.21, 119.65, 122.05, 122.95, 123.88, 126.81, 127.41, 128.42, 133.50, 133.64, 134.87, 135.09, 148.48, 150.87, 158.33, 182.85 (CO), 183.79 (CO).

Embodiment 15 (2-p-Tolyl-1H-anthra[1,2-d]imidazole-6,11-dione, No. 15)

All steps for manufacturing the to any compound No. 15 are identical with the steps of Embodiment 14, except that vanillin is substituted by ρ-tolualdehyde (0.7 ml, 5 mmol).

The compound No. 15 has the following characterstics: MW 338.1055 ($C_{22}H_{14}N_2O_4$); $R_f$: 0.65 (ethyl acetate:dichloromethane=1:4); IR (KBr) cm$^{-1}$: 3397 (NH), 1659 (CO); EI-MS m/z: 338 (M$^+$, 100%), 339 (24%) HRMS (ESI-TOF) m/z: calcd for $C_{22}H_{15}N_2O_4^+$ [M+H]$^+$: 339.1128, found: 339.1128; $^1$H-NMR (300 MHz, CDCl$_3$) δ (ppm): δ2.46 (3H, s, Ar'—CH$_3$), δ7.37 (2H, d, J=8.1 Hz, Ar'—$H_{3,5}$), δ7.79 (2H, t, J=3.6 Hz, Ar—$H_{7,10}$), δ8.03 (2H, d, J=7.8 Hz, Ar'—$H_{2,6}$), δ8.08 (1H, d, J=8.4 Hz, Ar—$H_5$), δ8.21 (1H, d, J=8.4 Hz, Ar—$H_4$), δ8.24-8.34 (2H, m, Ar—$H_{8,9}$), δ11.21 (1H, s, —NH); and $^{13}$C-NMR (75 MHz, CDCl$_3$) δ (ppm): 21.58, 117.89, 121.96, 125.44, 125.75, 126.46, 127.00, 127.58, 128.43, 130.00, 133.20, 133.26, 133.72, 133.99, 134.38, 142.05, 149.50, 156.86, 182.60 (CO), 185.16 (CO).

Embodiment 16 (2-(4-Bromophenyl)-1H-anthra[1,2-d]imidazole-6,11-dione, No. 16)

All steps for manufacturing the red brown compound No. 16 are identical with the steps of Embodiment 14, except that vanillin is substituted by 4-bromobenzaldehyde (0.93 g, 5 mmol).

The compound No. 16 has the following characterstics: MW 402.0004 ($C_{21}H_{11}N_2O_2Br$); $R_f$: 0.4 (ethyl acetate:dichloromethane=1:4); IR (KBr) cm$^{-1}$: 3391 (NH), 1658 (CO); EI-MS m/z 402 (M$^+$, 100%), 404 (97%), HRMS (ESI-TOF) m/z: calcd for $C_{21}H_{12}N_2O_2Br^+$ [M+H]$^+$: 403.0085, found: 403.0073 calcd for $C_{21}H_{10}N_2O_2Br^-$[M–H]$^-$: 400.9939, found: 400.9923; $^1$H-NMR (300 MHz, CDCl$_3$) δ (ppm): δ7.72 (2H, d, J=8.7 Hz, Ar'—$H_{3,5}$), δ7.80-7.83 (2H, m, Ar—$H_{7,10}$), δ8.06 (2H, d, J=8.7 Hz, Ar'—$H_{2,6}$), δ8.13 (1H, d, J=8.4 Hz, Ar—$H_4$), δ8.25 (1H, d, J=8.4 Hz, Ar—$H_5$), δ8.27-8.36 (2H, m, Ar—$H_{8,9}$), δ11.29 (1H, s, —NH); and $^{13}$C-NMR (75 MHz, CDCl$_3$) δ (ppm): 122.18, 125.86, 126.11, 126.57, 127.64, 127.69, 128.50, 128.89, 132.61, 133.20, 133.35, 133.87, 134.01, 134.57, 149.40, 155.62, 182.63 (CO), 185.25 (CO).

Embodiment 17 (2-(4-Cyanophenyl)-1H-anthra[1,2-d]imidazole-6,11-dione, No. 17)

All steps for manufacturing the yellowish brown compound No. 17 are identical with the steps of Embodiment 14, except that vanillin is substituted by 4-cyanobenzaldehyde (0.67 g, 5 mmol).

The compound No. 17 has the following characterstics: MW 349.0851 ($C_{22}H_{11}N_3O_2$); $R_f$: 0.65 (ethyl acetate:dichloromethane=1:4); IR (KBr) cm$^{-1}$: 3341 (NH), 2229 (CN), 1667 (CO); HRMS (ESI-TOF) m/z: calcd for $C_{22}H_{12}N_3O_2^+$ [M+H]$^+$: 350.0924, found: 350.0925; $^1$H-NMR (300 MHz, CDCl$_3$) δ (ppm): δ7.80-7.85 (2H, m, Ar—H$_{7,10}$), δ8.06 (2H, d, J=8.1 Hz, Ar—H$_{3',5'}$), δ8.18 (1H, d, J=8.4 Hz, Ar—H$_5$), δ8.27-8.32 (4H, m, Ar—H$_{4,8,2',6'}$), δ8.35-8.38 (1H, m, Ar—H$_9$), δ11.46 (1H, s, —NH); and $^{13}$C-NMR (75 MHz, DMSO-d$_6$) δ (ppm): 114.71, 118.04, 118.52, 122.39, 126.39, 126.63, 127.57, 127.75, 129.45, 132.76, 133.04, 133.11, 133.34, 133.93, 133.99, 134.70, 149.17, 154.25, 182.56 (CO), 185.21 (CO).

Embodiment 18 (2-(2,5-Dimethoxyphenyl)-1H-anthra[1,2-d]imidazole-6,11-dione, No. 18)

All steps for manufacturing the red brown compound No. 18 are identical with the steps of Embodiment 14, except that vanillin is substituted by 2,5-dimethoxybenzaldehyde (0.89 g, 5 mmol).

The compound No. 18 has the following characterstics: MW 384.1110 ($C_{23}H_{16}N_2O_4$); $R_f$: 0.4 (ethyl acetate:dichloromethane=1:4); IR (KBr) cm$^{-1}$: 3417 (NH), 1660 (C=O), 1226 (C—O); HRMS (ESI-TOF) m/z: calcd for $C_{23}H_{17}N_2O_4^+$ [M+H]$^+$: 385.1183, found: 385.1181; $^1$H-NMR (300 MHz, CDCl$_3$) δ (ppm): δ3.93 (3H, s, Ar$_5$—OCH$_3$), δ4.21 (H, s, Ar$_2$—OCH$_3$), 67 7.09 (2H, d, J=1.2 Hz, Ar—H$_{3',4'}$), δ7.79-7.82 (2H, m, Ar—H$_{7,10}$), δ8.13 (1H, d, J=8.1 Hz, Ar—H$_5$), δ8.13 (1H, s, Ar—H$_{6'}$), δ8.25 (1H, d, J=8.1 Hz, Ar—H$_4$), δ8.29-8.36 (2H, m, Ar—H$_{8,9}$), δ12.37 (1H, s, —NH); and $^{13}$C-NMR (75 MHz, CDCl$_3$) δ (ppm): 56.08, 56.69, 113.13, 113.36, 116.86, 118.14, 119.98, 121.92, 124.92, 126.46, 127.54, 129.92, 132.57, 133.43, 133.70, 134.06, 134.24, 135.39, 152.20, 154.23, 155.18, 182.82 (CO), 184.88 (CO).

Embodiment 19 (2-(Benzo[d][1,3]dioxol-5-yl)-1H-anthra[1,2-d]imidazole-6,11-dione, No. 19)

All steps for manufacturing the red brown compound No. 19 are identical with the steps of Embodiment 14, except that vanillin is substituted by piperonal (0.77 g, 5 mmol).

The compound No. 19 has the following characterstics: MW 368.0797 ($C_{22}H_{12}N_2O_4$); $R_f$: 0.45 (ethyl acetate:dichloromethane=1:4); IR (KBr) cm$^{-1}$: 3444 (NH), 1670 (C=O), 1257 (C—O), 1210 (C—O); HRMS (ESI-TOF) m/z: calcd for $C_{22}H_{13}N_2O_4^+$ [M+H]$^+$: 369.0867, found: 369.0887; $^1$H-NMR (300 MHz, CDCl$_3$) δ (ppm) δ6.11 (2H, s, —OCH$_2$O—), δ7.00 (1H, d, J=7.8 Hz, Ar—H$_{5'}$), δ7.67 (1H, s, Ar—H$_{2'}$), δ7.79-7.82 (2H, m, Ar—H$_{7,10}$), δ8.13 (1H, d, J=8.1 Hz, Ar—H$_5$), δ8.24 (1H, d, J=7.8 Hz, Ar—H$_{6'}$), δ8.25 (1H, d, J=8.1 Hz, Ar—H$_4$), δ8.29-8.36 (2H, m, Ar—H$_{8,9}$), δ11.18 (1H, s, —NH); and $^{13}$C-NMR (75 MHz, CDCl$_3$) δ (ppm): 101.93, 107.37, 108.96, 117.86, 121.83, 122.05, 122.78, 125.35, 126.52, 127.62, 128.40, 133.27, 133.43, 133.76, 134.08, 134.44, 148.71, 149.62, 150.56, 156.55, 182.66 (CO), 185.27 (CO).

Embodiment 20 (Anthra[2,1-c][1,2,5]thiadiazole-6,11-dione, No. 22)

1,2-Diaminoanthraquinone (1.19 g, 5 mmol) is dissolved in THF (30 mL), and triethylamine (3 mL) is further added thereinto for catalyzation after thionyl chloride (0.15 g, 20 mmol) is dripped thereinto. After mixing and reacting in room temperature for one hour, the reacted mixture is transferred into 200 mL of icy water. After filtering, the precipitate is collected and recrystallized by hot alcohol, so as to obtain yellow compound No. 22 with melting point of 227-228° C., and the production rate is 74%.

The compound No. 22 has the following characterstics: MW 266.0150 ($C_{14}H_6N_2O_2S$); $R_f$: 0.8 (ethyl acetate:dichloromethane=1:4); IR (KBr) cm$^{-1}$: 1671 (CO); EI-MS m/z: 210 (57%), 238 (64%), 266 (M$^+$, 100%), HRMS (ESI-TOF) m/z: calcd for $C_{14}H_7N_2O_2S^+$ [M+H]$^+$: 267.0223, found: 267.0226; $^1$H-NMR (300 MHz, CDCl$_3$) δ (ppm): δ7.84 (1H, dd, J=12.15, 6.9 Hz, Ar—H$_7$), δ7.85 (1H, dd, J=13.2, 7.5 Hz, Ar—H$_{10}$), δ8.33 (1H, dd, J=22.5, 7.2 Hz, Ar—H$_8$), δ8.33 (1H, dd, J=22.5, 7.2 Hz, Ar—H$_9$), δ8.41 (1H, d, J=9.3 Hz, Ar—H$_5$), δ8.56 (1H, d, J=9.3 Hz, Ar—H$_4$); and $^{13}$C-NMR (75 MHz, CDCl$_3$) δ (ppm): 125.07, 126.35, 126.99, 127.34, 127.61, 132.08, 133.47, 134.15, 134.75, 135.16, 150.93, 157.99, 181.97 (CO), 183.31 (CO).

Embodiment 21 (2,2-Dimethyl-2,3-dihydro-1H-anthra[1,2-d]imidazole-6,11-dione, No. 20)

1,2-Diaminoanthraquinone (1.19 g, 5 mmol) is dissolved in dry acetone (100 mL), and concentrated sulfuric acid (0.1 mL) is further added thereinto. After mixing and reacting in room temperature for 48 hours, the reacted mixture is transferred into a potassium carbonate column. The product is collected and recrystallized by methanol, so as to obtain the purple compound 20, and the production rate is 31%. In the purification steps of the Embodiment 21, regular extraction method will reduce the production rate, and thus the basic column is used to remove the acid in the rough extract, so as to increase the production rate.

The compound No. 20 has the following characterstics: Melting point: 235-237□, MW 278.1055 ($C_{17}H_{14}N_2O_2$); $R_f$: 0.5 (ethyl acetate:dichloromethane=1:4); IR (KBr) cm$^{-1}$: 3419 (NH), 3239 (NH), 1639 (CO); EI-MS m/z: 263 (100%), 278 (M$^+$, 8.6%), HRMS (ESI-TOF) m/z: calcd for $C_{17}H_{15}N_2O_2^+$ [M+H]$^+$: 279.1128, found: 279.1133; $^1$H-NMR (300 MHz, DMSO-d$_6$) δ (ppm): δ1.48 (6H, s, —CH$_3$), δ6.26 (1H, d, J=7.8 Hz, Ar—H$_4$), δ7.37 (1H, d, J=7.8 Hz, Ar—H$_5$), δ7.73-7.76 (m, 2H, Ar—H$_{7,10}$), δ8.05 (s, 1H, —NHC—), δ8.08-8.12 (m, 2H, Ar—H$_{8,9}$), δ8.79 (s, 1H, —CNH—); and $^{13}$C-NMR (75 MHz, DMSO-d$_6$) δ (ppm): 30.18, 81.70, 104.02, 108.04, 120.99, 123.54, 126.32, 127.07, 133.41, 133.54, 134.79, 135.46, 143.05, 148.12, 179.89 (CO), 182.47 (CO).

Embodiment 22 (2-Methyl-2-phenyl-2,3-dihydro-1H-anthra[1,2-d]imidazole-6,11-dione, No. 21)

1,2-Diaminoanthraquinone (1.19 g, 5 mmol) is dissolved in N,N-dimethylformamide (30 mL), and concentrated sulfuric acid (0.1 mL) is further added thereinto after acetophenone (0.5 ml, 6 mmol) is added thereinto. After mixing and reacting in room temperature for 72 hours, the reacted mixture is transferred into icy water (200 mL) for precipitation. The precipitate is collected and recrystallized by hot alcohol, so as to obtain the black compound 21, and the production rate is 28%.

The compound No. 21 has the following characterstics: Melting point: 368-371□, MW 340.1212 ($C_{22}H_{16}N_2O_2$); $R_f$: 0.8 (ethyl acetate:dichloromethane=1:4); IR (KBr) cm$^{-1}$: 3348 (NH), 1671 (CO); HRMS (ESI-TOF) m/z: calcd for $C_{22}H_{17}N_2O_2^+$ [M+H]$^+$: 341.1284, found: 341.1033; $^1$H-NMR (300 MHz, DMSO-d$_6$) δ (ppm): δ1.22 (3H, s, —CH$_3$), δ7.56-7.62 (3H, m, Ar'—H$_{2,4,6}$), δ7.90-7.94 (2H, m, Ar—H$_{7,10}$), δ8.08 (1H, d, J=8.1 Hz, Ar—H$_5$), δ8.22 (1H, d, J=8.1 Hz, Ar—H$_4$), δ8.18-8.22 (2H, m, Ar'—H$_{3,5}$), δ8.40-8.42 (2H, m, Ar—H$_{8,9}$); and $^{13}$C-NMR (75 MHz, DMSO) δ (ppm): 28.79, 83.56, 103.62, 109.74, 119.13, 121.35, 124.03, 126.20, 1267.76, 128.32, 128.77, 131.31, 132.99, 134.30, 134.45, 143.05, 157.25, 182.60 (CO), 182.89 (CO).

Embodiment 23 (2,3-dimethylnaphtho[2,3-f]quinoxaline-7,12-dione, No. 24)

1,2-Diaminoanthraquinone (1.19 g, 5 mmol) is dissolved in N,N-dimethylformamide (30 mL), and concentrated sulfuric acid (0.1 mL) is further added thereinto after methyl vinyl ketone (0.36 g, 5 mmol) is added thereinto. After mixing and reacting in room temperature for 72 hours, the reacted mixture is transferred into icy water (200 mL) for precipitation. The precipitate is collected and recrystallized by hot alcohol, so as to obtain the black compound 24, and the production rate is 25%.

The compound No. 24 has the following characterstics: Melting point >400☐, MW 288.0899 ($C_{18}H_{12}N_2O_2$); $R_f$: 0.6 (ethyl acetate:dichloromethane=1:4); IR (KBr) cm$^{-1}$: 1671 (CO); HRMS (ESI-TOF) m/z: calcd for $C_{18}H_{13}N_2O_2^+$ [M+H]$^+$: 289.0988, found: 289.0970; $^1$H-NMR (300 MHz, DMSO-d$_6$) δ (ppm): δ2.72 (3H, s, —CH$_3$), δ2.88 (3H, s, —CH$_3$), δ7.91-7.94 (2H, m, Ar—H$_{8,11}$), δ8.07 (1H, d, J=8.4 Hz, Ar—H$_5$), δ8.16 (1H, d, J=8.4 Hz, Ar—H$_4$), δ8.19-8.21 (2H, m, Ar—H$_{9,10}$); and $^{13}$C-NMR (75 MHz, DMSO-d$_6$) δ (ppm): 14.91, 30.74, 120.19, 125.46, 126.21, 126.26, 127.16, 128.18, 128.87, 133.01, 133.10, 134.19, 134.27, 134.42, 158.87, 162.28, 182.49 (CO), 183.37 (CO).

Embodiment 24 (Naphtho[2,3-f]quinoxaline-7,12-dione, No. 25)

1,2-Diaminoanthraquinone (1.19 g, 5 mmol) is dissolved in N,N-dimethylformamide (30 mL), and 40% glyoxal (0.8 g, 5 mml) in EtOH (50 mL) is added thereinto. After reverse flow for 16 hours, the water is evaporated out, and the reacted mixture is transferred into icy water (200 mL) for precipitation. The precipitate is collected and washed by hot alcohol and dichloromethane repeatedly, so as to obtain the black compound 25, and the production rate is 23%.

The compound No. 25 has the following characterstics: Melting point: 270-272 ☐, MW 260.0586 ($C_{16}H_8N_2O_2$); $R_f$: 0.45 (ethyl acetate:dichloromethane=1:4); IR (KBr) cm$^{-1}$: 3413 (NH), 3365 (NH), 1626 (CO); EI-MS m/z: 150 (54%), 238 (73%), 260 (M$^+$, 100%); HRMS (ESI-TOF) m/z: calcd for $C_{16}H_9N_2O_2^+$ [M+H]$^+$: 261.0659, found: 261.0663; $^1$H-NMR (300 MHz, CDCl$_3$) δ (ppm): δ7.82-7.87 (2H, m, Ar—H$_{8,11}$), δ8.29-8.36 (2H, m, Ar—H$_{9,10}$), δ8.48 (1H, d, J=8.7 Hz, Ar—H$_5$), δ8.72 (1H, d, J=8.7 Hz, Ar—H$_6$), δ8.99 (1H, d, J=1.5 Hz, —N═CH—), δ9.25 (1H, d, J=1.5 Hz, —CH═N—); and $^{13}$C-NMR (75 MHz, CDCl$_3$) δ (ppm): 126.72, 127.05, 127.46, 130.05, 131.98, 133.77, 134.76, 135.18, 135.88, 135.93, 136.03, 145.42, 146.40, 147.77, 183.21 (CO), 183.61 (CO).

Embodiment 25 (Naphtho[2,3-f]quinoxaline-2,3,7,12(1H,4H)-tetraone, No. 26)

1,2-Diaminoanthraquinone (1.19 g, 5 mmol) is dissolved in N,N-dimethylformamide (30 mL), and oxalic acid (0.46 g, 5 mmol) and concentrated sulfuric acid (0.1 mL) is added thereinto. After reverse flow for 16 hours, the reacted mixture is transferred into icy water (200 mL) for precipitation. The precipitate is collected and washed by hot alcohol and, so as to obtain the black compound 26, and the production rate is 30%.

The compound No. 25 has the following characteristics: Melting point: 245-246 ☐, MW 292.0484 ($C_{16}H_8N_2O_4$); $R_f$: 0.25 (ethyl acetate:dichloromethane=1:4); IR (KBr) cm$^{-1}$: 1710 (CO), 1671 (CONH); EI-MS m/z: 248 (100%), 292 (M$^+$) HRMS (ESI-TOF) m/z: calcd for $C_{16}H_9N_2O_4^+$ [M+H]$^+$: 293.0557, found: 293.0568; $^1$H-NMR (300 MHz, DMSO-d$_6$) δ (ppm): δ7.71 (1H, d, J=8.0 Hz, Ar—H$_5$), δ7.93-7.98 (2H, m, Ar—H$_{8,11}$), δ8.04 (1H, d, J=8.0 Hz, Ar—H$_6$), δ8.17-8.24 (2H, m, Ar—H$_{9,10}$), δ8.99 (1H, d, J=1.5 Hz, —NH—), δ9.25 (1H, d, J=1.5 Hz, —NH—); and $^{13}$C-NMR (75 MHz, DMSO-d$_6$) δ (ppm); 118.08, 120.52, 122.87, 126.26, 126.34, 126.78, 127.71, 128.17, 129.58, 134.48, 134.55, 135.07, 154.64 (NHCO), 154.73 (NHCO), 180.08 (CO), 181.07(CO).

The chemical formula, production rates and melting points of the above-mentioned heteroannelated anthraquinone derivatives of series A are illustrated in Table 1, and the chemical formula, production rates and melting points of the above-mentioned heteroannelated anthraquinone derivatives of series B, C and D are described in the embodiments, respectively.

TABLE 1

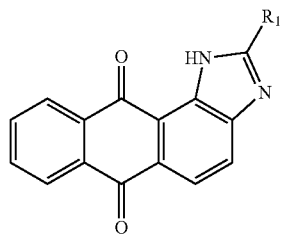

| Compound No. | $R_1$ | Melting point (☐) | Production Rate (%) |
|---|---|---|---|
| 2 | —CH$_3$ | >400 | 67 |
| 3 | —CH$_2$Cl | 272-273 | 86 |
| 4 | —CH$_2$CH$_3$ | 193-194 | 39 |
| 5 | —CH(CH$_3$)$_2$ | 199-200 | 41 |
| 6 | —(CH$_2$)$_3$CH$_3$ | 192-193 | –36 |
| 7 | —CH(CH$_3$)CH$_2$CH$_3$ | 118-119 | 40 |
| 8 | —CH(CH$_3$)$_3$ | 209-210 | 37 |
| 9 | —(CH$_2$)$_6$CH$_3$ | 85-87 | 38 |
| 10 | —CH═CHCH$_2$CH$_3$ | 117-119 | 33 |
| 11 | —C$_6$H$_5$ | 232-233 | 74 |
| 12 | —C$_6$H$_4$-p-N(CH$_3$)$_2$ | 239-241 | 79 |
| 13 | —C$_6$H$_4$-p-NO$_2$ | 342-343 | 89 |
| 14 | —C$_6$H$_3$-p-OH-m-OCH$_3$ | 230-231 | 47 |
| 15 | —C$_6$H$_4$-p-CH$_3$ | 256-257 | 76 |
| 16 | —C$_6$H$_4$-p-Br | 302-303 | 75 |
| 17 | —C$_6$H$_4$-p-CN | 353-354 | 77 |
| 18 | —C$_6$H$_3$-o,m-(OCH$_3$)$_2$ | 251-252 | 74 |
| 19 | 3,4-benzdioxole | 300-301 | 81 |

Telomeric repeat amplification protocol (TRAP) is employed to detect the effect of the heteroannelated anthraquinone derivatives synthesized in the present invention for inhibiting the telomerase activity. In the first stage of this method, the telemerase is used to prolong the oligonucleotide with telomere sequence in the conditions of 90° C. for 10 minutes, 72° C. for 3 minutes, 50° C. for 60 seconds and 94° C. for 30 seconds (TSG4 primer: 5'-GGG ATT GGG ATT GGG ATT GGG TT-3') In the second stage, different compounds are added into the telomerase reacted product to further replicate the telomere product by PCR (CX primer: 5'-CCCTTA CCCTTA CCCTTA CCCTAA-3'). When the compound inhibits the telomerase activity, the replication reaction can not be resumed. The PCR conditions includes 39 cycles of PCR reaction in 50° C. for 30 seconds, 72° C. for 60 seconds for 39 PCR cycles, followed by one cycle of reaction in 94° C. for 30 seconds, 50° C. for 30 seconds, 72° C. for 30 seconds and 72° C. for 1 minute, and the reaction is ended in 4° C. The PCR product is analyzed by electrophoresis using 10% acrylamide gel. In the electrophoresis results, the positive control (P) is sterile water (dddH$_2$O), and the negative control (N) is 5 μl 0.1 mg/mL RNase A (CLONTECH). The positive control (P) produces lots of telomere fragment, while the negative control (N) does not. The compounds provided by the present invention inhibit the telomerase activity by stabilizing G-quadruplex structures and blocking the interaction between telomerase and telomere, or directly inhibit the telomerase activity, so as to inhibit the prolongation of telomere. It is found in the present experiments that the Embodiments A4 and A5 have better inhibition effects.

In addition, it is found in the in vitro experiments performed by the development therapeutics program of US cancer research center that the heteroannelated anthraquinone derivatives synthesized in the present invention have various inhibition effects on different cancer cell lines at $1.0 \times 10^{-5}$ molal concentration (M) as shown in Table 2. For example, the Embodiment A2 of the present invention inhibits the growth of breast cancer cell HS578T, and the Embodiment B1 has overall and the most obvious inhibition on different cancer cells. Therefore, the heteroannelated anthraquinone derivatives synthesized in the present invention are potential drugs for inhibiting cancer cells.

TABLE 2

|  | No. 22 | No. 4 | No. 20 | No. 25 | No. 26 |
|---|---|---|---|---|---|
| Non-small cell lung cancer cell |  |  |  |  |  |
| HOP-62 | −100.00 | 97.73 | XXX | XXX | XXX |
| HOP-92 | XXX | 41.43 | 5.10 | XXX | −15.08 |
| Colorectal cancer cell |  |  |  |  |  |
| HCC-2998 | −50.00 | 67.67 | 136.96 | −7.15 | 77.59 |
| Breast cancer cell |  |  |  |  |  |
| HS 578T | −7.40 | −18.58 | XXX | XXX | XXX |
| MCF7 | −50.74 | 69.82 | 83.58 | 39.68 | 85.17 |
| MDA-MB-435 | −87.88 | 84.39 | 124.56 | 102.03 | 144.42 |
| MDA-MB-468 | −73.17 | XXX | 77.25 | 75.28 | 38.35 |
| T-47D | −45.52 | 63.05 | 82.96 | 85.19 | 87.10 |
| Ovary cancer cell |  |  |  |  |  |
| IGROV1 | −88.34 | XXX | −2.80 | 3.44 | 13.36 |
| OVCAR-4 | −94.43 | 48.81 | 80.14 | 94.22 | 103.31 |
| Blood cancer cell |  |  |  |  |  |
| MOLT-4 | −40.09 | 64.17 | 116.41 | 22.91 | 121.52 |
| Kidney cancer cell |  |  |  |  |  |
| ACHN | −94.31 | 24.97 | 50.17 | 46.52 | 81.33 |
| SN12C | −73.27 | 68.53 | 91.98 | 64.65 | 94.07 |
| UO-31 | −79.30 | 23.94 | 30.65 | 51.45 | 61.43 |
| Skin cancer cell |  |  |  |  |  |
| LOX IMV1 | −50.6 | 39.98 | 61.88 | 44.18 | 96.94 |
| MALME-3M | −71.54 | 56.94 | 155.47 | 180.88 | 149.83 |
| SK-MEL-2 | −73.16 | 40.07 | 8.04 | 6.66 | 21.96 |
| UACC-257 | −83.07 | 39.69 | 118.22 | 91.06 | 118.21 |
| UACC-62 | −82.32 | 51.35 | 67.58 | 90.47 | 95.25 |
| CNS cancer cell |  |  |  |  |  |
| SF-539 | −47.11 | 83.16 | 93.56 | 40.72 | 101.16 |
| U251 | −89.26 | 60.13 | 87.84 | 63.47 | 95.92 |
| Mean | 2.68 | 58.42 | 80.41 | 69.36 | 100.83 |

TABLE 2-continued

|  | No. 22 | No. 4 | No. 20 | No. 25 | No. 26 |
|---|---|---|---|---|---|
| Delta | 102.68 | 77.00 | 83.21 | 76.51 | 115.91 |
| Range | 230.09 | 120.88 | 158.27 | 188.03 | 289.23 | xxx: not detected

The detailed in-vitro testing results of dose response of the Compound No. 22 obtained from National Cancer Institute Developmental Therapeutics Program are shown in Tables 3-1 to 3-9.

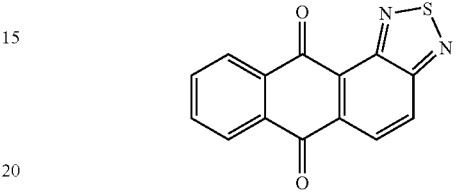

The detailed in-vitro testing results of dose response of the Compound No. 4 obtained from National Cancer Institute Developmental Therapeutics Program are shown in Tables 4-1 to 4-9.

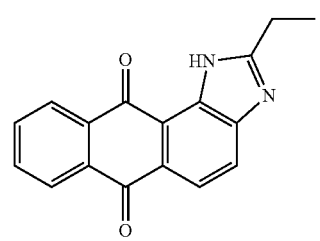

The detailed in-vitro testing results of dose response of the Compound No. 25 obtained from National Cancer Institute Developmental Therapeutics Program are shown in Tables 5-1 to 5-9.

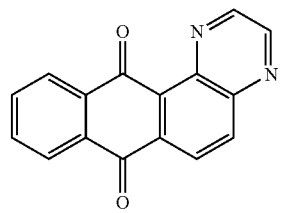

TABLE 3-1

| Panel/Cell Line | Time |  | Mean Optical Densities |  |  |  |  |  | Log10 Concentration |  |  |  |  | GI50 | TGI | LC50 |
|---|---|---|---|---|---|---|---|---|---|---|---|---|---|---|---|---|
|  |  |  |  |  |  |  |  |  | Percent Growth |  |  |  |  |  |  |  |
|  | Zero | Ctrl | −8.0 | −7.0 | −6.0 | −5.0 | −4.0 | −8.0 | −7.0 | −6.0 | −5.0 | −4.0 |  |  |  |  |
| Leukemia |  |  |  |  |  |  |  |  |  |  |  |  |  |  |  |  |
| CCRF-CEM | 0.445 | 1.624 | 1.589 | 1.503 | 1.323 | 0.472 | 0.470 | 97 | 90 | 74 | 2 | 2 | 2.18E−6 | >1.00E−4 | >1.00E−4 |
| HL-60(TB) | 0.744 | 2.175 | 2.214 | 2.209 | 2.079 | 0.461 | 0.421 | 103 | 102 | 93 | −38 | −43 | 2.14E−6 | 5.13E−6 | >1.00E−4 |
| K-562 | 0.180 | 1.220 | 1.232 | 1.174 | 1.038 | 0.375 | 0.165 | 101 | 96 | 83 | 19 | −8 | 3.23E−6 | 4.92E−5 | >1.00E−4 |
| MOLT-4 | 0.455 | 1.447 | 1.444 | 1.462 | 1.199 | 0.274 | 0.280 | 97 | 99 | 73 | −40 | −38 | 1.59E−6 | 4.43E−6 | >1.00E−4 |
| RPMI-8226 | 0.654 | 1.899 | 1.899 | 1.820 | 1.418 | 0.653 | 0.523 | 100 | 94 | 61 | . | −20 | 1.53E−6 | 9.91E−6 | >1.00E−4 |
| SR | 0.167 | 0.676 | 0.718 | 0.738 | 0.669 | 0.374 | 0.278 | 108 | 112 | 99 | 41 | −22 | 6.89E−6 | >1.00E−4 | >1.00E−4 |

TABLE 3-2

| Panel/Cell Line | | | Log10 Concentration | | | | | | | | | | | | | |
|---|---|---|---|---|---|---|---|---|---|---|---|---|---|---|---|---|
| Non-Small Cell | Time | | Mean Optical Densities | | | | | Percent Growth | | | | | | | | |
| Lung Cancer | Zero | Ctrl | -8.0 | -7.0 | -6.0 | -5.0 | -4.0 | -8.0 | -7.0 | -6.0 | -5.0 | -4.0 | GI50 | TGI | LC50 |
| A549/ATCC | 0.110 | 0.550 | 0.566 | 0.518 | 0.513 | 0.081 | 0.091 | 104 | 93 | 92 | -27 | -18 | 2.25E-6 | 5.94E-6 | >1.00E-4 |
| EKVX | 0.652 | 1.960 | 1.914 | 1.813 | 1.745 | 0.554 | 0.251 | 96 | 89 | 84 | -15 | -62 | 2.19E-6 | 7.03E-6 | 5.65E-5 |
| HOP-62 | 0.342 | 1.187 | 1.242 | 1.242 | 1.243 | 0.380 | 0.175 | 107 | 107 | 107 | 4 | -49 | 3.59E-6 | 1.21E-5 | >1.00E-4 |
| HOP-92 | 0.770 | 1.201 | 1.179 | 1.150 | 1.174 | 0.765 | 0.560 | 95 | 88 | 94 | -1 | -27 | 2.91E-6 | 9.84E-6 | >1.00E-4 |
| NCI-H226 | 1.003 | 1.740 | 1.718 | 1.701 | 1.556 | 1.467 | 0.956 | 97 | 95 | 75 | 63 | -5 | 1.56E-5 | 8.53E-5 | >1.00E-4 |
| NCI-H23 | 0.418 | 1.199 | 1.209 | 1.125 | 0.775 | 0.265 | 0.271 | 101 | 91 | 46 | -37 | -35 | 8.02E-7 | 3.59E-6 | >1.00E-4 |
| NCI-H322M | 0.347 | 0.840 | 0.856 | 0.922 | 0.940 | 0.890 | 0.555 | 103 | 116 | 120 | 110 | 42 | 7.64E-5 | >1.00E-4 | >1.00E-4 |
| NCI-H460 | 0.245 | 1.818 | 1.818 | 1.767 | 1.614 | 0.116 | 0.104 | 100 | 97 | 87 | -53 | -58 | 1.84E-6 | 4.19E-6 | 9.54E-6 |
| NCI-H522 | 0.541 | 2.032 | 2.079 | 2.073 | 1.887 | 0.634 | 0.441 | 103 | 103 | 90 | 6 | -18 | 3.01E-6 | 1.78E-5 | >1.00E-4 |

TABLE 3-3

| Panel/Cell Line | | | Log10 Concentration | | | | | | | | | | | | | |
|---|---|---|---|---|---|---|---|---|---|---|---|---|---|---|---|---|
| | Time | | Mean Optical Densities | | | | | Percent Growth | | | | | | | | |
| Colon Cancer | Zero | Ctrl | -8.0 | -7.0 | -6.0 | -5.0 | -4.0 | -8.0 | -7.0 | -6.0 | -5.0 | -4.0 | GI50 | TGI | LC50 |
| COLO 205 | 0.199 | 0.969 | 0.927 | 0.872 | 0.957 | 0.069 | 0.057 | 95 | 87 | 98 | -66 | -71 | 1.97E-6 | 3.98E-6 | 8.04E-6 |
| HCC-2998 | 0.268 | 0.572 | 0.599 | 0.581 | 0.588 | 0.098 | 0.081 | 109 | 103 | 105 | -63 | -70 | 2.12E-6 | 4.20E-6 | 8.32E-6 |
| HCT-116 | 0.138 | 0.938 | 0.927 | 0.912 | 0.863 | 0.145 | 0.095 | 99 | 97 | 91 | 1 | -31 | 2.84E-6 | 1.06E-5 | >1.00E-4 |
| HCT-15 | 0.285 | 1.440 | 1.554 | 1.485 | 1.323 | 0.254 | 0.138 | 110 | 104 | 90 | -11 | -52 | 2.49E-6 | 7.80E-6 | 9.06E-6 |
| HT29 | 0.231 | 1.387 | 1.432 | 1.444 | 1.403 | 0.195 | 0.108 | 104 | 105 | 101 | -16 | -53 | 2.75E-6 | 7.36E-6 | 8.10E-5 |
| KM12 | 0.217 | 0.841 | 0.884 | 0.889 | 0.861 | 0.567 | 0.103 | 107 | 108 | 103 | 56 | -53 | 1.14E-5 | 3.28E-5 | 9.48E-5 |
| SW-620 | 0.175 | 1.174 | 1.231 | 1.201 | 1.240 | 0.633 | 0.056 | 106 | 103 | 107 | 46 | -68 | 8.55E-6 | 2.52E-5 | 6.92E-5 |

TABLE 3-4

| Panel/Cell Line | | | Log10 Concentration | | | | | | | | | | | | | |
|---|---|---|---|---|---|---|---|---|---|---|---|---|---|---|---|---|
| | Time | | Mean Optical Densities | | | | | Percent Growth | | | | | | | | |
| CNS Cancer | Zero | Ctrl | -8.0 | -7.0 | -6.0 | -5.0 | -4.0 | -8.0 | -7.0 | -6.0 | -5.0 | -4.0 | GI50 | TGI | LC50 |
| SF-268 | 0.357 | 0.951 | 0.959 | 0.938 | 0.893 | 0.459 | 0.193 | 101 | 98 | 90 | 17 | -46 | 3.55E-6 | 1.87E-5 | >1.00E-4 |
| SF-295 | 0.415 | 1.524 | 1.550 | 1.579 | 1.527 | 0.404 | 0.202 | 102 | 105 | 100 | -3 | -51 | 3.08E-6 | 9.40E-6 | 9.39E-5 |
| SF-539 | 0.574 | 1.690 | 1.578 | 1.517 | 1.499 | 0.006 | 0.012 | 90 | 84 | 83 | -99 | -98 | 1.52E-6 | 2.86E-6 | 5.38E-6 |
| SNB-19 | 0.464 | 1.328 | 1.349 | 1.339 | 1.330 | 0.067 | 0.008 | 102 | 101 | 100 | -86 | -98 | 1.86E-6 | 3.46E-6 | 6.43E-6 |
| SNB-75 | 0.640 | 1.050 | 0.950 | 0.911 | 0.957 | -0.004 | -0.009 | 76 | 66 | 77 | -100 | -100 | 1.42E-6 | 2.73E-6 | 5.22E-6 |
| U251 | 0.220 | 1.137 | 1.194 | 1.177 | 0.939 | 0.086 | 0.082 | 106 | 104 | 78 | -61 | -63 | 1.60E-6 | 3.65E-6 | 8.32E-6 |

TABLE 3-5

| Panel/Cell Line | | | Log10 Concentration | | | | | | | | | | | | | |
|---|---|---|---|---|---|---|---|---|---|---|---|---|---|---|---|---|
| | Time | | Mean Optical Densities | | | | | Percent Growth | | | | | | | | |
| Melanoma | Zero | Ctrl | -8.0 | -7.0 | -6.0 | -5.0 | -4.0 | -8.0 | -7.0 | -6.0 | -5.0 | -4.0 | GI50 | TGI | LC50 |
| LOX IMVI | 0.363 | 2.033 | 2.046 | 2.006 | 1.219 | 0.212 | 0.244 | 101 | 98 | 51 | -42 | -33 | 1.03E-6 | 3.56E-6 | >1.00E-4 |
| MALME-3M | 0.229 | 0.481 | 0.487 | 0.520 | 0.512 | 0.107 | 0.065 | 102 | 115 | 112 | -53 | -72 | 2.37E-6 | 4.76E-6 | 9.55E-6 |
| M14 | 0.339 | 1.395 | 1.398 | 1.394 | 1.411 | 0.232 | 0.199 | 100 | 100 | 102 | -32 | -41 | 2.44E-6 | 5.78E-6 | >1.00E-4 |
| SK-MEL-2 | 0.284 | 0.761 | 0.810 | 0.806 | 0.731 | 0.221 | 0.194 | 110 | 109 | 94 | -22 | -32 | 2.38E-6 | 6.42E-6 | >1.00E-4 |
| SK-MEL-28 | 0.300 | 1.110 | 1.135 | 1.161 | 1.165 | 0.703 | 0.023 | 103 | 106 | 107 | 50 | -93 | 9.88E-6 | 2.24E-5 | 5.03E-5 |
| SK-MEL-5 | 0.540 | 2.145 | 2.107 | 1.896 | 1.477 | -0.009 | -0.002 | 98 | 85 | 58 | -100 | -100 | 1.13E-6 | 2.34E-6 | 4.83E-6 |
| UACC-257 | 0.493 | 0.980 | 0.962 | 0.986 | 0.870 | 0.083 | 0.047 | 96 | 101 | 77 | -83 | -91 | 1.48E-6 | 3.03E-6 | 6.21E-6 |
| UACC-62 | 0.431 | 1.918 | 1.751 | 1.787 | 1.798 | 0.331 | 0.214 | 89 | 91 | 92 | -23 | -50 | 2.31E-6 | 6.29E-6 | 9.62E-6 |

TABLE 3-6

| Panel/Cell Line | Time | | Mean Optical Densities | | | | | Percent Growth | | | | | | | |
|---|---|---|---|---|---|---|---|---|---|---|---|---|---|---|---|
| | | | Log10 Concentration | | | | | Log10 Concentration | | | | | | | |
| Ovarian Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| OVCAR-3 | 0.305 | 0.775 | 0.852 | 0.821 | 0.710 | 0.216 | 0.075 | 116 | 110 | 86 | −29 | −75 | 2.06E−6 | 5.59E−6 | 2.82E−5 |
| OVCAR-4 | 0.363 | 0.880 | 0.916 | 0.850 | 0.531 | −0.015 | −0.014 | 107 | 94 | 32 | −100 | −100 | 5.20E−7 | 1.76E−6 | 4.19E−6 |
| OVCAR-5 | 0.446 | 0.930 | 0.924 | 0.903 | 0.953 | 0.192 | 0.187 | 99 | 94 | 105 | −57 | −58 | 2.18E−6 | 4.44E−6 | 9.06E−6 |
| OVCAR-8 | 0.299 | 1.154 | 1.200 | 1.171 | 0.695 | 0.169 | 0.185 | 105 | 102 | 46 | −43 | −38 | 8.59E−7 | 3.28E−6 | >1.00E−4 |
| SK-OV-3 | 0.530 | 1.224 | 1.239 | 1.154 | 1.150 | 0.414 | 0.015 | 102 | 90 | 89 | −22 | −97 | 2.26E−6 | 6.35E−6 | 2.36E−5 |

TABLE 3-7

| Panel/Cell Line | Time | | Mean Optical Densities | | | | | Percent Growth | | | | | | | |
|---|---|---|---|---|---|---|---|---|---|---|---|---|---|---|---|
| | | | Log10 Concentration | | | | | Log10 Concentration | | | | | | | |
| Renal Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| 786-0 | 0.450 | 1.828 | 1.894 | 1.916 | 2.049 | 0.517 | 0.130 | 105 | 106 | 116 | 5 | −71 | 3.93E−6 | 1.16E−5 | 5.27E−5 |
| A498 | 0.605 | 1.481 | 1.527 | 1.518 | 1.449 | 1.479 | 1.340 | 105 | 104 | 96 | 100 | 84 | >1.00E−4 | >1.00E−4 | >1.00E−4 |
| ACHN | 0.355 | 1.317 | 1.389 | 1.452 | 1.220 | 0.063 | 0.218 | 107 | 114 | 90 | −82 | −39 | 1.71E−6 | 3.33E−6 | . |
| CAKI-1 | 0.294 | 0.870 | 0.813 | 0.844 | 0.798 | 0.226 | 0.099 | 90 | 95 | 88 | −23 | −66 | 2.18E−6 | 6.16E−6 | 4.15E−5 |
| SN12C | 0.304 | 1.076 | 1.007 | 1.097 | 0.948 | 0.284 | 0.199 | 91 | 103 | 83 | −7 | −35 | 2.35E−6 | 8.42E−6 | >1.00E−4 |
| TK-10 | 0.362 | 0.792 | 0.865 | 0.935 | 0.983 | 0.868 | 0.337 | 117 | 133 | 144 | 118 | −7 | 3.49E−5 | 8.80E−5 | >1.00E−4 |
| UO-31 | 0.147 | 0.498 | 0.539 | 0.562 | 0.499 | 0.041 | 0.050 | 111 | 118 | 100 | −72 | −66 | 1.95E−6 | 3.81E−6 | 7.41E−6 |

TABLE 3-8

| Panel/Cell Line | Time | | Mean Optical Densities | | | | | Percent Growth | | | | | | | |
|---|---|---|---|---|---|---|---|---|---|---|---|---|---|---|---|
| | | | Log10 Concentration | | | | | Log10 Concentration | | | | | | | |
| Prostate Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| PC-3 | 0.372 | 1.158 | 1.128 | 1.096 | 1.050 | 0.459 | 0.402 | 96 | 92 | 86 | 11 | 4 | 3.03E−6 | >1.00E−4 | >1.00E−4 |
| DU-145 | 0.230 | 0.704 | 0.750 | 0.772 | 0.752 | 0.425 | −0.002 | 110 | 114 | 110 | 41 | −100 | 7.41E−6 | 1.95E−5 | 4.42E−5 |

TABLE 3-9

| Panel/Cell Line | Time | | Mean Optical Densities | | | | | Percent Growth | | | | | | | |
|---|---|---|---|---|---|---|---|---|---|---|---|---|---|---|---|
| | | | Log10 Concentration | | | | | Log10 Concentration | | | | | | | |
| Breast Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| MCF7 | 0.282 | 1.325 | 1.202 | 1.081 | 0.929 | 0.101 | 0.104 | 88 | 77 | 62 | −64 | −63 | 1.24E−6 | 3.10E−6 | 7.72E−6 |
| NCI/ADR-RES | 0.436 | 1.282 | 1.343 | 1.296 | 0.608 | 0.395 | 0.363 | 107 | 102 | 20 | −10 | −17 | 4.32E−7 | 4.80E−6 | >1.00E−4 |
| MDA-MB-231/ATCC | 0.478 | 1.197 | 1.226 | 1.100 | 1.063 | 0.510 | 0.525 | 104 | 87 | 81 | 4 | 6 | 2.56E−6 | >1.00E−4 | >1.00E−4 |
| HS 578T | 0.413 | 1.287 | 1.362 | 1.410 | 1.289 | 0.663 | 0.595 | 109 | 114 | 100 | 29 | 21 | 5.03E−6 | >1.00E−4 | >1.00E−4 |
| MDA-MB-435 | 0.280 | 1.351 | 1.350 | 1.373 | 1.160 | 0.190 | 0.137 | 100 | 102 | 82 | −32 | −51 | 1.91E−6 | 5.23E−6 | 8.78E−5 |
| BT-549 | 0.254 | 0.524 | 0.503 | 0.529 | 0.594 | 0.426 | 0.122 | 92 | 102 | 126 | 64 | −52 | 1.31E−5 | 3.55E−5 | 9.62E−5 |
| T-47D | 0.377 | 0.816 | 0.775 | 0.763 | 0.473 | 0.156 | 0.150 | 91 | 88 | 22 | −59 | −60 | 3.75E−7 | 1.87E−6 | 7.79E−6 |
| MDA-MB-468 | 2.275 | 3.124 | 3.096 | 3.134 | 3.152 | 0.022 | 0.031 | 97 | 101 | 103 | −99 | −99 | 1.83E−6 | 3.24E−6 | 5.72E−6 |

TABLE 4-1

| Panel/Cell Line | Time | | Mean Optical Densities | | | | | Percent Growth | | | | | | | |
|---|---|---|---|---|---|---|---|---|---|---|---|---|---|---|---|
| | | | Log10 Concentration | | | | | Log10 Concentration | | | | | | | |
| Leukemia | Zero | Ctrl | −8.0 | −7.0 | −6.0 | −5.0 | −4.0 | −8.0 | −7.0 | −6.0 | −5.0 | −4.0 | GI50 | TGI | LC50 |
| CCRF-CEM | 0.321 | 1.468 | 1.505 | 1.400 | 1.407 | 0.910 | 0.488 | 103 | 94 | 95 | 51 | 15 | 1.09E−5 | >1.00E−4 | >1.00E−4 |
| HL-60(TB) | 0.691 | 1.628 | 1.626 | 1.630 | 1.639 | 1.092 | 0.873 | 100 | 100 | 101 | 43 | 19 | 7.53E−6 | >1.00E−4 | >1.00E−4 |
| K-562 | 0.269 | 1.578 | 1.498 | 1.469 | 1.412 | 1.097 | 0.903 | 94 | 92 | 87 | 63 | 48 | 7.83E−5 | >1.00E−4 | >1.00E−4 |
| MOLT-4 | 0.734 | 2.108 | 2.076 | 2.057 | 2.015 | 1.402 | 0.726 | 98 | 96 | 93 | 49 | −1 | 9.31E−6 | 9.51E−5 | >1.00E−4 |
| RPMI-8226 | 0.443 | 1.284 | 1.259 | 1.121 | 1.060 | 0.547 | 0.390 | 97 | 81 | 73 | 12 | −12 | 2.42E−6 | 3.21E−5 | >1.00E−4 |

TABLE 4-2

| Panel/Cell Line Non-Small Cell Lung Cancer | Time | | Mean Optical Densities | | | | | | Percent Growth | | | | | | |
|---|---|---|---|---|---|---|---|---|---|---|---|---|---|---|---|
| | | | Log10 Concentration | | | | | | Log10 Concentration | | | | | | |
| | Zero | Ctrl | -8.0 | -7.0 | -6.0 | -5.0 | -4.0 | -8.0 | -7.0 | -6.0 | -5.0 | -4.0 | GI50 | TGI | LC50 |
| A549/ATCC | 0.193 | 0.895 | 0.832 | 0.892 | 0.876 | 0.614 | 0.315 | 91 | 100 | 97 | 60 | 17 | 1.71E-5 | >1.00E-4 | >1.00E-4 |
| EKVX | 0.897 | 1.986 | 1.856 | 1.792 | 1.540 | 1.059 | 0.894 | 88 | 82 | 59 | 15 | . | 1.60E-6 | 9.43E-5 | >1.00E-4 |
| HOP-62 | 0.474 | 1.375 | 1.283 | 1.318 | 1.254 | 1.127 | 0.814 | 90 | 94 | 87 | 72 | 38 | 4.42E-5 | >1.00E-4 | >1.00E-4 |
| HOP-92 | 0.892 | 1.397 | 1.360 | 1.297 | 1.214 | 1.134 | 1.010 | 93 | 80 | 64 | 48 | 23 | 7.38E-6 | >1.00E-4 | >1.00E-4 |
| NCI-H226 | 0.817 | 1.747 | 1.612 | 1.642 | 1.608 | 1.404 | 1.022 | 85 | 89 | 85 | 63 | 22 | 2.08E-5 | >1.00E-4 | >1.00E-4 |
| NCI-H23 | 0.485 | 1.638 | 1.547 | 1.500 | 1.333 | 1.051 | 0.732 | 92 | 88 | 74 | 49 | 21 | 9.17E-6 | >1.00E-4 | >1.00E-4 |
| NCI-H322M | 0.721 | 1.844 | 1.757 | 1.746 | 1.643 | 1.177 | 0.976 | 92 | 91 | 82 | 41 | 23 | 5.94E-6 | >1.00E-4 | >1.00E-4 |
| NCI-H460 | 0.233 | 1.933 | 1.666 | 1.630 | 1.494 | 0.651 | 0.266 | 84 | 82 | 74 | 25 | 2 | 3.07E-6 | >1.00E-4 | >1.00E-4 |
| NCI-H522 | 0.713 | 2.605 | 2.403 | 2.370 | 2.360 | 1.735 | 1.328 | 89 | 88 | 87 | 54 | 32 | 1.54E-5 | >1.00E-4 | >1.00E-4 |

TABLE 4-3

| Panel/Cell Line Colon Cancer | Time | | Mean Optical Densities | | | | | | Percent Growth | | | | | | |
|---|---|---|---|---|---|---|---|---|---|---|---|---|---|---|---|
| | | | Log10 Concentration | | | | | | Log10 Concentration | | | | | | |
| | Zero | Ctrl | -8.0 | -7.0 | -6.0 | -5.0 | -4.0 | -8.0 | -7.0 | -6.0 | -5.0 | -4.0 | GI50 | TGI | LC50 |
| COLO 205 | 0.213 | 1.012 | 0.960 | 0.958 | 0.891 | 0.544 | 0.284 | 93 | 93 | 85 | 41 | 9 | 6.36E-6 | >1.00E-4 | >1.00E-4 |
| HCC-2998 | 0.660 | 2.134 | 1.963 | 2.044 | 1.983 | 1.527 | 0.988 | 88 | 94 | 90 | 59 | 22 | 1.74E-5 | >1.00E-4 | >1.00E-4 |
| HCT-116 | 0.248 | 2.129 | 1.969 | 2.043 | 1.716 | 1.044 | 0.450 | 92 | 95 | 78 | 42 | 11 | 6.10E-6 | >1.00E-4 | >1.00E-4 |
| HCT-15 | 0.248 | 1.514 | 1.391 | 1.422 | 1.121 | 0.588 | 0.348 | 90 | 93 | 69 | 27 | 8 | 2.82E-6 | >1.00E-4 | >1.00E-4 |
| HT29 | 0.151 | 0.999 | 0.951 | 0.998 | 0.893 | 0.557 | 0.241 | 94 | 100 | 88 | 48 | 11 | 8.84E-6 | >1.00E-4 | >1.00E-4 |
| KM12 | 0.268 | 1.092 | 1.072 | 1.040 | 1.003 | 0.625 | 0.373 | 98 | 94 | 89 | 43 | 13 | 7.15E-6 | >1.00E-4 | >1.00E-4 |
| SW-620 | 0.150 | 0.998 | 0.991 | 0.968 | 0.902 | 0.480 | 0.202 | 99 | 96 | 89 | 39 | 6 | 5.97E-6 | >1.00E-4 | >1.00E-4 |

TABLE 4-4

| Panel/Cell Line CNS Cancer | Time | | Mean Optical Densities | | | | | | Percent Growth | | | | | | |
|---|---|---|---|---|---|---|---|---|---|---|---|---|---|---|---|
| | | | Log10 Concentration | | | | | | Log10 Concentration | | | | | | |
| | Zero | Ctrl | -8.0 | -7.0 | -6.0 | -5.0 | -4.0 | -8.0 | -7.0 | -6.0 | -5.0 | -4.0 | GI50 | TGI | LC50 |
| SF-268 | 0.319 | 1.084 | 0.986 | 1.053 | 0.990 | 0.758 | 0.530 | 87 | 96 | 88 | 57 | 28 | 1.77E-5 | >1.00E-4 | >1.00E-4 |
| SF-295 | 0.695 | 1.929 | 1.785 | 1.806 | 1.549 | 1.127 | 0.812 | 88 | 90 | 69 | 35 | 9 | 3.65E-6 | >1.00E-4 | >1.00E-4 |
| SF-539 | 0.639 | 1.878 | 1.642 | 1.666 | 1.631 | 1.204 | 0.798 | 81 | 83 | 80 | 46 | 13 | 7.46E-6 | >1.00E-4 | >1.00E-4 |
| SNB-19 | 0.656 | 1.341 | 1.229 | 1.299 | 1.289 | 1.073 | 0.921 | 84 | 94 | 92 | 61 | 39 | 3.09E-5 | >1.00E-4 | >1.00E-4 |
| SNB-75 | 0.661 | 1.282 | 1.068 | 1.070 | 0.965 | 0.916 | 0.770 | 66 | 66 | 49 | 41 | 17 | 8.72E-7 | >1.00E-4 | >1.00E-4 |
| U251 | 0.280 | 1.443 | 1.369 | 1.393 | 1.260 | 0.854 | 0.597 | 94 | 96 | 84 | 49 | 27 | 9.58E-6 | >1.00E-4 | >1.00E-4 |

TABLE 4-5

| Panel/Cell Line Melanoma | Time | | Mean Optical Densities | | | | | | Percent Growth | | | | | | |
|---|---|---|---|---|---|---|---|---|---|---|---|---|---|---|---|
| | | | Log10 Concentration | | | | | | Log10 Concentration | | | | | | |
| | Zero | Ctrl | -8.0 | -7.0 | -6.0 | -5.0 | -4.0 | -8.0 | -7.0 | -6.0 | -5.0 | -4.0 | GI50 | TGI | LC50 |
| LOX IMVI | 0.316 | 2.231 | 2.245 | 2.058 | 1.903 | 0.956 | 0.508 | 101 | 91 | 83 | 33 | 10 | 4.61E-6 | >1.00E-4 | >1.00E-4 |
| MALME-3M | 0.694 | 1.247 | 1.174 | 1.161 | 1.153 | 0.835 | 0.683 | 87 | 84 | 83 | 26 | -2 | 3.75E-6 | 8.69E-5 | >1.00E-4 |
| M14 | 0.435 | 1.796 | 1.627 | 1.731 | 1.500 | 1.119 | 0.776 | 88 | 95 | 78 | 50 | 25 | 1.02E-5 | >1.00E-4 | >1.00E-4 |
| SK-MEL-28 | 0.239 | 0.861 | 0.794 | 0.762 | 0.730 | 0.537 | 0.211 | 89 | 84 | 79 | 48 | -12 | 8.58E-6 | 6.36E-5 | >1.00E-4 |
| SK-MEL-5 | 0.639 | 2.089 | 1.284 | 1.249 | 1.501 | 0.607 | 0.515 | 44 | 42 | 59 | -5 | -19 | . | 8.36E-6 | >1.00E-4 |
| UACC-257 | 0.437 | 0.825 | 0.763 | 0.761 | 0.808 | 0.694 | 0.506 | 84 | 84 | 96 | 66 | 18 | 2.16E-5 | >1.00E-4 | >1.00E-4 |
| UACC-62 | 0.639 | 2.092 | 1.844 | 1.978 | 1.874 | 1.231 | 1.015 | 83 | 92 | 85 | 41 | 26 | 6.18E-6 | >1.00E-4 | >1.00E-4 |

TABLE 4-6

| Panel/Cell Line | Time | Mean Optical Densities | | | | | | Percent Growth | | | | | | | |
|---|---|---|---|---|---|---|---|---|---|---|---|---|---|---|---|
| | | | | Log10 Concentration | | | | | | Log10 Concentration | | | | | |
| Ovarian Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| IGROV1 | 0.518 | 1.681 | 1.555 | 1.537 | 1.174 | 0.583 | 0.421 | 89 | 88 | 56 | 6 | −19 | 1.34E−6 | 1.69E−5 | >1.00E−4 |
| OVCAR-3 | 0.283 | 0.746 | 0.745 | 0.773 | 0.713 | 0.549 | 0.319 | 100 | 106 | 93 | 57 | 8 | 1.41E−5 | >1.00E−4 | >1.00E−4 |
| OVCAR-4 | 0.565 | 1.740 | 1.719 | 1.694 | 1.535 | 0.999 | 0.745 | 98 | 96 | 83 | 37 | 15 | 5.18E−6 | >1.00E−4 | >1.00E−4 |
| OVCAR-5 | 0.395 | 0.931 | 0.865 | 0.884 | 0.900 | 0.852 | 0.637 | 88 | 91 | 94 | 85 | 45 | 7.57E−5 | >1.00E−4 | >1.00E−4 |
| OVCAR-8 | 0.228 | 0.904 | 0.881 | 0.841 | 0.847 | 0.623 | 0.393 | 96 | 91 | 92 | 58 | 24 | 1.77E−5 | >1.00E−4 | >1.00E−4 |
| SK-OV-3 | 0.566 | 1.432 | 1.392 | 1.359 | 1.223 | 0.673 | 0.687 | 95 | 92 | 76 | 12 | 14 | 2.55E−6 | >1.00E−4 | >1.00E−4 |

TABLE 4-7

| Panel/Cell Line | Time | Mean Optical Densities | | | | | | Percent Growth | | | | | | | |
|---|---|---|---|---|---|---|---|---|---|---|---|---|---|---|---|
| | | | | Log10 Concentration | | | | | | Log10 Concentration | | | | | |
| Renal Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| 786-0 | 0.664 | 2.228 | 2.288 | 2.259 | 2.143 | 1.725 | 1.264 | 104 | 102 | 95 | 68 | 38 | 4.02E−5 | >1.00E−4 | >1.00E−4 |
| A498 | 0.564 | 1.224 | 1.202 | 1.221 | 1.065 | 0.793 | 0.453 | 94 | 97 | 74 | 34 | −20 | 3.89E−6 | 4.27E−5 | >1.00E−4 |
| ACHN | 0.385 | 1.455 | 1.393 | 1.299 | 1.047 | 0.537 | 0.366 | 94 | 85 | 62 | 14 | −5 | 1.77E−6 | 5.46E−5 | >1.00E−4 |
| CAKI-1 | 0.547 | 1.711 | 1.680 | 1.610 | 1.430 | 0.780 | 0.654 | 97 | 91 | 76 | 20 | 9 | 2.90E−6 | >1.00E−4 | >1.00E−4 |
| SN12C | 0.617 | 1.996 | 1.639 | 1.719 | 1.640 | 1.247 | 0.872 | 74 | 80 | 74 | 46 | 18 | 7.05E−6 | >1.00E−4 | >1.00E−4 |
| TK-10 | 0.612 | 1.245 | 1.212 | 1.327 | 1.088 | 0.856 | 0.633 | 95 | 113 | 75 | 39 | 3 | 4.88E−6 | >1.00E−4 | >1.00E−4 |
| UO-31 | 0.517 | 1.634 | 1.496 | 1.444 | 1.268 | 0.680 | 0.518 | 88 | 83 | 67 | 15 | . | 2.12E−6 | >1.00E−4 | >1.00E−4 |

TABLE 4-8

| Panel/Cell Line | Time | Mean Optical Densities | | | | | | Percent Growth | | | | | | | |
|---|---|---|---|---|---|---|---|---|---|---|---|---|---|---|---|
| | | | | Log10 Concentration | | | | | | Log10 Concentration | | | | | |
| Prostate Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| PC-3 | 0.306 | 1.233 | 1.197 | 1.233 | 1.170 | 0.807 | 0.572 | 96 | 100 | 93 | 54 | 29 | 1.44E−5 | >1.00E−4 | >1.00E−4 |
| DU-145 | 0.226 | 0.724 | 0.713 | 0.713 | 0.666 | 0.411 | 0.344 | 98 | 98 | 88 | 37 | 24 | 5.62E−6 | >1.00E−4 | >1.00E−4 |

TABLE 4-9

| Panel/Cell Line | Time | Mean Optical Densities | | | | | | Percent Growth | | | | | | | |
|---|---|---|---|---|---|---|---|---|---|---|---|---|---|---|---|
| | | | | Log10 Concentration | | | | | | Log10 Concentration | | | | | |
| Breast Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| MCF7 | 0.249 | 1.082 | 0.960 | 0.880 | 0.697 | 0.556 | 0.240 | 85 | 76 | 54 | 37 | −4 | 1.68E−6 | 8.14E−5 | >1.00E−4 |
| NCI/ADR-RES | 0.461 | 1.540 | 1.483 | 1.524 | 1.421 | 1.010 | 0.530 | 95 | 99 | 89 | 51 | 6 | 1.05E−5 | >1.00E−4 | >1.00E−4 |
| MDA-MB-231/ATCC | 0.453 | 1.133 | 1.121 | 1.097 | 1.063 | 0.820 | 0.700 | 98 | 95 | 90 | 54 | 36 | 1.66E−5 | >1.00E−4 | >1.00E−4 |
| HS 578T | 0.296 | 0.704 | 0.734 | 0.736 | 0.526 | 0.393 | 0.202 | 107 | 108 | 56 | 24 | −32 | 1.56E−6 | 2.67E−5 | >1.00E−4 |
| MDA-MB-435 | 0.515 | 1.859 | 1.815 | 1.744 | 1.748 | 1.404 | 1.019 | 97 | 91 | 92 | 66 | 37 | 3.65E−5 | >1.00E−4 | >1.00E−4 |
| BT-549 | 1.015 | 2.001 | 2.009 | 2.006 | 1.951 | 1.606 | 1.166 | 101 | 100 | 95 | 60 | 15 | 1.67E−5 | >1.00E−4 | >1.00E−4 |
| T-47D | 0.415 | 0.852 | 0.876 | 0.824 | 0.755 | 0.554 | 0.459 | 105 | 94 | 78 | 32 | 10 | 4.00E−6 | >1.00E−4 | >1.00E−4 |
| MDA-MB-468 | 0.494 | 1.038 | 0.944 | 0.977 | 0.923 | 0.654 | 0.458 | 83 | 89 | 79 | 29 | −7 | 3.83E−6 | 6.33E−5 | >1.00E−4 |

TABLE 5-1

| Panel/Cell Line | Time | Mean Optical Densities | | | | | | Percent Growth | | | | | | | |
|---|---|---|---|---|---|---|---|---|---|---|---|---|---|---|---|
| | | | | Log10 Concentration | | | | | | Log10 Concentration | | | | | |
| Leukemia | Zero | Ctrl | −8.0 | −7.0 | −6.0 | −5.0 | −4.0 | −8.0 | −7.0 | −6.0 | −5.0 | −4.0 | GI50 | TGI | LC50 |
| CCRF-CEM | 0.230 | 0.806 | 0.751 | 0.755 | 0.622 | 0.358 | 0.344 | 90 | 91 | 68 | 22 | 20 | 2.46E−6 | >1.00E−4 | >1.00E−4 |
| HL-60(TB) | 0.336 | 0.640 | 0.587 | 0.540 | 0.478 | 0.347 | 0.153 | 83 | 67 | 47 | 3 | −54 | 6.77E−7 | 1.15E−5 | 8.37E−5 |
| K-562 | 0.086 | 0.900 | 0.851 | 0.422 | 0.332 | 0.225 | 0.166 | 94 | 41 | 30 | 17 | 10 | 6.83E−8 | >1.00E−4 | >1.00E−4 |
| MOLT-4 | 0.273 | 1.048 | 0.959 | 0.900 | 0.830 | 0.529 | 0.302 | 89 | 81 | 72 | 33 | 4 | 3.65E−6 | >1.00E−4 | >1.00E−4 |
| RPMI-8226 | 0.429 | 1.331 | 1.245 | 1.161 | 0.926 | 0.702 | 0.535 | 90 | 81 | 55 | 30 | 12 | 1.61E−6 | >1.00E−4 | >1.00E−4 |

TABLE 5-2

| Panel/Cell Line | | | Log10 Concentration | | | | | | | | | | | | |
|---|---|---|---|---|---|---|---|---|---|---|---|---|---|---|---|
| Non-Small Cell | Time | | Mean Optical Densities | | | | | Percent Growth | | | | | | | |
| Lung Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| A549/ATCC | 0.551 | 1.857 | 1.771 | 1.792 | 1.552 | 1.022 | 0.594 | 93 | 95 | 77 | 36 | 3 | 4.53E−6 | >1.00E−4 | >1.00E−4 |
| EKVX | 0.439 | 1.025 | 1.032 | 0.960 | 0.904 | 0.584 | 0.421 | 101 | 89 | 79 | 25 | −4 | 3.45E−6 | 7.21E−5 | >1.00E−4 |
| HOP-62 | 0.233 | 0.934 | 0.879 | 0.811 | 0.799 | 0.512 | 0.255 | 92 | 82 | 81 | 40 | 3 | 5.64E−6 | >1.00E−4 | >1.00E−4 |
| HOP-92 | 0.785 | 1.360 | 1.334 | 1.260 | 1.231 | 1.206 | 0.829 | 95 | 83 | 78 | 73 | 8 | 2.25E−5 | >1.00E−4 | >1.00E−4 |
| NCI-H226 | 0.780 | 1.765 | 1.631 | 1.577 | 1.497 | 1.415 | 0.769 | 86 | 81 | 73 | 64 | −1 | 1.66E−5 | 9.52E−5 | >1.00E−4 |
| NCI-H23 | 0.452 | 1.356 | 1.281 | 1.242 | 1.213 | 0.950 | 0.407 | 92 | 87 | 84 | 55 | −10 | 1.20E−5 | 7.03E−5 | >1.00E−4 |
| NCI-H322M | 0.310 | 0.751 | 0.736 | 0.709 | 0.722 | 0.592 | 0.307 | 96 | 90 | 93 | 64 | −1 | 1.63E−5 | 9.61E−5 | >1.00E−4 |
| NCI-H460 | 0.229 | 1.901 | 1.869 | 1.815 | 1.309 | 0.507 | 0.179 | 98 | 95 | 65 | 17 | −22 | 2.01E−6 | 2.69E−5 | >1.00E−4 |
| NCI-H522 | 0.336 | 1.040 | 0.966 | 0.942 | 0.906 | 0.579 | 0.226 | 89 | 86 | 81 | 35 | −33 | 4.64E−6 | 3.25E−5 | >1.00E−4 |

TABLE 5-3

| Panel/Cell Line | | | Log10 Concentration | | | | | | | | | | | | |
|---|---|---|---|---|---|---|---|---|---|---|---|---|---|---|---|
| | Time | | Mean Optical Densities | | | | | Percent Growth | | | | | | | |
| Colon Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| COLO 205 | 0.211 | 0.782 | 0.739 | 0.704 | 0.634 | 0.376 | 0.138 | 92 | 86 | 74 | 29 | −35 | 3.40E−6 | 2.84E−5 | >1.00E−4 |
| HCC-2998 | 0.326 | 1.161 | 1.135 | 1.113 | 0.759 | 0.658 | 0.315 | 97 | 94 | 52 | 40 | −3 | 1.40E−6 | 8.35E−5 | >1.00E−4 |
| HCT-116 | 0.142 | 1.101 | 1.060 | 1.089 | 1.018 | 0.666 | 0.175 | 96 | 99 | 91 | 55 | 3 | 1.23E−5 | >1.00E−4 | >1.00E−4 |
| HCT-15 | 0.274 | 1.667 | 1.502 | 1.449 | 1.343 | 0.784 | 0.266 | 88 | 84 | 77 | 37 | −3 | 4.63E−6 | 8.43E−5 | >1.00E−4 |
| HT29 | 0.174 | 1.186 | 1.176 | 1.131 | 0.925 | 0.636 | 0.184 | 99 | 95 | 74 | 46 | 1 | 7.01E−6 | >1.00E−4 | >1.00E−4 |
| KM12 | 0.224 | 0.967 | 0.884 | 0.896 | 0.786 | 0.522 | 0.185 | 89 | 90 | 76 | 40 | −18 | 5.26E−6 | 4.95E−5 | >1.00E−4 |
| SW-620 | 0.159 | 1.008 | 0.960 | 0.901 | 0.649 | 0.369 | 0.118 | 94 | 87 | 58 | 25 | −26 | 1.71E−6 | 3.08E−5 | >1.00E−4 |

TABLE 5-4

| Panel/Cell Line | | | Log10 Concentration | | | | | | | | | | | | |
|---|---|---|---|---|---|---|---|---|---|---|---|---|---|---|---|
| | Time | | Mean Optical Densities | | | | | Percent Growth | | | | | | | |
| CNS Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| SF-268 | 0.347 | 1.080 | 1.051 | 1.020 | 0.981 | 0.598 | 0.357 | 96 | 92 | 86 | 34 | 1 | 4.98E−6 | >1.00E−4 | >1.00E−4 |
| SF-295 | 0.598 | 1.530 | 1.440 | 1.375 | 1.481 | 0.828 | 0.456 | 90 | 83 | 95 | 25 | −24 | 4.35E−6 | 3.23E−5 | >1.00E−4 |
| SF-539 | 0.657 | 1.869 | 1.748 | 1.719 | 1.430 | 0.937 | 0.601 | 90 | 88 | 64 | 23 | −9 | 2.18E−6 | 5.37E−5 | >1.00E−4 |
| SNB-19 | 0.279 | 0.934 | 0.892 | 0.887 | 0.867 | 0.650 | 0.307 | 94 | 93 | 90 | 57 | 4 | 1.34E−5 | >1.00E−4 | >1.00E−4 |
| SNB-75 | 0.649 | 1.457 | 1.324 | 1.350 | 1.264 | 1.079 | 0.740 | 83 | 87 | 76 | 53 | 11 | 1.19E−5 | >1.00E−4 | >1.00E−4 |
| U251 | 0.231 | 1.283 | 1.242 | 1.205 | 1.172 | 0.604 | 0.184 | 96 | 93 | 89 | 35 | −21 | 5.38E−6 | 4.29E−5 | >1.00E−4 |

TABLE 5-5

| Panel/Cell Line | | | Log10 Concentration | | | | | | | | | | | | |
|---|---|---|---|---|---|---|---|---|---|---|---|---|---|---|---|
| | Time | | Mean Optical Densities | | | | | Percent Growth | | | | | | | |
| Melanoma | Zero | Ctrl | −8.0 | −7.0 | −6.0 | −5.0 | −4.0 | −8.0 | −7.0 | −6.0 | −5.0 | −4.0 | GI50 | TGI | LC50 |
| LOX IMVI | 0.311 | 2.100 | 1.927 | 1.830 | 1.766 | 0.867 | 0.244 | 90 | 85 | 81 | 31 | −22 | 4.20E−6 | 3.89E−5 | >1.00E−4 |
| MALME-3M | 0.403 | 0.725 | 0.715 | 0.696 | 0.687 | 0.498 | 0.145 | 97 | 91 | 88 | 30 | −64 | 4.48E−6 | 2.07E−5 | 7.08E−5 |
| M14 | 0.352 | 1.249 | 1.202 | 1.164 | 1.149 | 0.659 | 0.356 | 95 | 91 | 89 | 34 | . | 5.14E−6 | >1.00E−4 | >1.00E−4 |
| SK-MEL-2 | 0.212 | 0.515 | 0.505 | 0.471 | 0.521 | 0.388 | 0.171 | 97 | 85 | 102 | 58 | −20 | 1.27E−5 | 5.59E−5 | >1.00E−4 |
| SK-MEL-28 | 0.363 | 1.041 | 1.041 | 1.050 | 1.070 | 0.873 | 0.352 | 100 | 101 | 104 | 75 | −3 | 2.10E−5 | 9.11E−5 | >1.00E−4 |
| SK-MEL-5 | 0.644 | 2.455 | 2.270 | 2.280 | 2.136 | 1.150 | 0.049 | 90 | 90 | 82 | 28 | −92 | 3.93E−6 | 1.71E−5 | 4.44E−5 |
| UACC-257 | 0.466 | 1.070 | 1.040 | 0.996 | 1.063 | 0.815 | 0.413 | 95 | 88 | 99 | 58 | −11 | 1.30E−5 | 6.83E−5 | >1.00E−4 |
| UACC-62 | 0.828 | 2.206 | 2.103 | 1.986 | 2.030 | 1.655 | 0.662 | 92 | 84 | 87 | 60 | −20 | 1.33E−5 | 5.61E−5 | >1.00E−4 |

TABLE 5-6

| Panel/Cell Line | Time | Mean Optical Densities | | | | | | Percent Growth | | | | | | | |
|---|---|---|---|---|---|---|---|---|---|---|---|---|---|---|---|
| | | | | Log10 Concentration | | | | | | Log10 Concentration | | | | | |
| Ovarian Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| IGROV1 | 0.313 | 1.001 | 0.932 | 0.824 | 0.735 | 0.543 | 0.229 | 90 | 74 | 61 | 33 | −27 | 2.55E−6 | 3.59E−5 | >1.00E−4 |
| OVCAR-3 | 0.237 | 0.743 | 0.766 | 0.717 | 0.626 | 0.260 | 0.137 | 104 | 95 | 77 | 4 | −42 | 2.34E−6 | 1.25E−5 | >1.00E−4 |
| OVCAR-4 | 0.449 | 1.297 | 1.311 | 1.220 | 1.075 | 0.883 | 0.472 | 102 | 91 | 74 | 51 | 3 | 1.05E−5 | >1.00E−4 | >1.00E−4 |
| OVCAR-5 | 0.372 | 1.072 | 1.054 | 0.999 | 1.056 | 0.912 | 0.506 | 97 | 90 | 98 | 77 | 19 | 5.93E−5 | >1.00E−4 | >1.00E−4 |
| OVCAR-8 | 0.271 | 1.191 | 1.163 | 1.091 | 1.031 | 0.606 | 0.390 | 97 | 89 | 83 | 36 | 13 | 5.07E−6 | >1.00E−4 | >1.00E−4 |
| SK-OV-3 | 0.521 | 1.313 | 1.243 | 1.228 | 1.150 | 0.874 | 0.586 | 91 | 89 | 79 | 44 | 8 | 6.95E−6 | >1.00E−4 | >1.00E−4 |

TABLE 5-7

| Panel/Cell Line | Time | Mean Optical Densities | | | | | | Percent Growth | | | | | | | |
|---|---|---|---|---|---|---|---|---|---|---|---|---|---|---|---|
| | | | | Log10 Concentration | | | | | | Log10 Concentration | | | | | |
| Renal Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| 786-0 | 0.611 | 2.118 | 2.089 | 2.131 | 2.186 | 1.320 | 0.835 | 98 | 101 | 104 | 47 | 15 | 8.87E−6 | >1.00E−4 | >1.00E−4 |
| A498 | 0.575 | 1.116 | 1.079 | 1.034 | 1.058 | 0.839 | 0.456 | 93 | 85 | 89 | 49 | −21 | 9.31E−6 | 5.03E−5 | >1.00E−4 |
| ACHN | 0.370 | 1.672 | 1.642 | 1.508 | 1.367 | 0.776 | 0.397 | 98 | 87 | 77 | 31 | 2 | 3.85E−6 | >1.00E−4 | >1.00E−4 |
| CAKI-1 | 0.369 | 1.388 | 1.325 | 1.271 | 1.260 | 0.762 | 0.409 | 94 | 89 | 87 | 39 | 4 | 5.83E−6 | >1.00E−4 | >1.00E−4 |
| RXF 393 | 0.826 | 2.065 | 2.024 | 1.973 | 1.829 | 1.355 | 0.919 | 97 | 93 | 81 | 43 | 7 | 6.43E−6 | >1.00E−4 | >1.00E−4 |
| SN12C | 0.518 | 1.551 | 1.421 | 1.257 | 1.326 | 1.108 | 0.508 | 87 | 71 | 78 | 57 | −2 | 1.32E−5 | 9.27E−5 | >1.00E−4 |
| TK-10 | 0.190 | 0.513 | 0.518 | 0.464 | 0.457 | 0.306 | 0.196 | 102 | 85 | 83 | 36 | 2 | 5.00E−6 | >1.00E−4 | >1.00E−4 |
| UO-31 | 0.483 | 1.268 | 1.113 | 1.058 | 1.059 | 0.678 | 0.475 | 80 | 73 | 73 | 25 | −2 | 3.02E−6 | 8.59E−5 | >1.00E−4 |

TABLE 5-8

| Panel/Cell Line | Time | Mean Optical Densities | | | | | | Percent Growth | | | | | | | |
|---|---|---|---|---|---|---|---|---|---|---|---|---|---|---|---|
| | | | | Log10 Concentration | | | | | | Log10 Concentration | | | | | |
| Prostate Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| PC-3 | 0.138 | 0.476 | 0.479 | 0.449 | 0.373 | 0.306 | 0.308 | 101 | 92 | 69 | 50 | 50 | . | >1.00E−4 | >1.00E−4 |
| DU-145 | 0.200 | 0.762 | 0.775 | 0.735 | 0.739 | 0.515 | 0.103 | 102 | 95 | 96 | 56 | −49 | 1.14E−5 | 3.43E−5 | >1.00E−4 |

TABLE 5-9

| Panel/Cell Line | Time | Mean Optical Densities | | | | | | Percent Growth | | | | | | | |
|---|---|---|---|---|---|---|---|---|---|---|---|---|---|---|---|
| | | | | Log10 Concentration | | | | | | Log10 Concentration | | | | | |
| Breast Cancer | Zero | Ctrl | −8.0 | −7.0 | −6.0 | −5.0 | −4.0 | −8.0 | −7.0 | −6.0 | −5.0 | −4.0 | GI50 | TGI | LC50 |
| MCF7 | 0.451 | 2.118 | 1.797 | 1.793 | 1.201 | 0.894 | 0.318 | 81 | 80 | 45 | 27 | −29 | 7.22E−7 | 2.98E−5 | >1.00E−4 |
| NCI/ADR-RES | 0.476 | 1.685 | 1.621 | 1.586 | 1.530 | 0.934 | 0.567 | 95 | 92 | 87 | 38 | 8 | 5.68E−6 | >1.00E−4 | >1.00E−4 |
| MDA-MB-231/ATCC | 0.444 | 1.084 | 1.085 | 1.008 | 0.987 | 0.854 | 0.535 | 100 | 88 | 85 | 64 | 14 | 1.91E−5 | >1.00E−4 | >1.00E−4 |
| HS 578T | 0.415 | 0.913 | 0.854 | 0.861 | 0.819 | 0.710 | 0.405 | 88 | 90 | 81 | 59 | −2 | 1.41E−5 | 9.14E−5 | >1.00E−4 |
| MDA-MB-435 | 0.426 | 1.511 | 1.527 | 1.479 | 1.525 | 1.043 | 0.021 | 101 | 97 | 101 | 57 | −95 | 1.11E−5 | 2.37E−5 | 5.04E−5 |
| BT-549 | 0.571 | 1.144 | 1.114 | 1.057 | 1.044 | 0.886 | 0.562 | 95 | 85 | 83 | 55 | −2 | 1.22E−5 | 9.35E−5 | >1.00E−4 |
| T-47D | 0.393 | 0.891 | 0.819 | 0.794 | 0.747 | 0.674 | 0.362 | 85 | 80 | 71 | 56 | −8 | 1.26E−5 | 7.51E−5 | >1.00E−4 |

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

Citations:

1. Bestilny, L. J.; Brown, C. B.; Miura, Y.; Robertson, L. D.; Riabowol, K. T. Selective inhibition of telomerase activity during terminal differentiation of immortal cell lines. *Cancer Res.* 1996, 56, 3796-802.
2. Bodnar, A. G.; Ouellette, M.; Frolkis, M.; Holt, S. E.; Chiu, C. P.; Morin, G. B.; Harley, C. B.; Shay, J. W.; Lichtsteiner, S.; Wright, W. E. Extension of life-span by introduction of telomerase into normal human cells. *Science.* 1998, 279, 349-52.
3. Urquidi, V.; Tarin, D.; Goodison, S. Role of telomerase in cell senescence and oncogenesis. *Annu. Rev. Med.* 2000, 51, 65-79.
4. Smogorzewska, A.; de Lange, T. Regulation of telomerase by telomeric proteins. *Annu. Rev. Biochem.* 2004, 73, 177-208.
5. Peng, X.; Wu, Y.; Fan, J.; Tian, M.; Han, K. Colorimetric and ratiometric fluorescence sensing of fluoride: tuning selectivity in proton transfer. *J. Org. Chem.* 2005, 70, 10524-31.

What is claimed is:

1. A compound of formula (I):

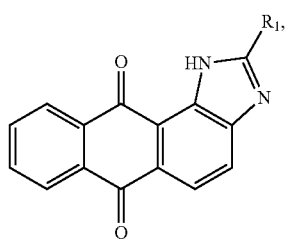

wherein $R_1$ is selected from the group consisting of:
i) amino, nitro and cyano;
ii) $(CH_2)_nX$, $CH_2F$, $CH_2Br$, $CH_2I$, straight $C_6$-$C_{12}$ alkyl, $C_5$-$C_7$ alkyl, $C_1$-$C_{12}$ alkoxy, unsubstituted $C_3$-$C_{12}$ cycloalkyl, $C_{1-5}$ alkyl $C_3$-$C_{12}$ cycloalkyl, $C_3$-$C_4$ cycloalkoxy and $C_3$-$C_{12}$ cycloalkyl substituted with at least one subtituent selected from the group consisting of straight or branched $C_1$-$C_{12}$ alkyl, amino, nitro, cyano, straight or branched $C_1$-$C_{12}$ haloalkyl, $C_1$-$C_5$ alkoxy, $C_1$-$C_5$ haloalkoxy, $C_3$-$C_5$ cycloalkoxy and $C_3$-$C_5$ halocycloalkoxy, wherein X is a halogen and n is 2, 3, 4, 5, 6, 7, 8, 9, 10, 11 or 12;
iii) straight $C_2$-$C_8$ alkenyl, $C_1$-$C_3$ alkyl $C_2$-$C_5$ alkenyl, $C_2$-$C_8$ alkenyloxy, $C_2$-$C_8$ haloalkenyl, $C_3$-$C_8$ cycloalkenyl and $C_1$-$C_3$ alkyl $C_3$-$C_8$ cycloalkenyl; and
iv) unsubstituted $C_5$ heterocyclyl, unsubstituted $C_7$-$C_{12}$ heterocyclyl and $C_5$-$C_{12}$ heterocyclyl substituted with at least one subtituent selected from the group consisting of straight or branched $C_1$-$C_{12}$ alkyl, amino, nitro, cyano, straight or branched $C_1$-$C_{12}$ haloalkyl, $C_1$-$C_5$ alkoxy, $C_1$-$C_5$ haloalkoxy, $C_3$-$C_5$ cycloalkoxy and $C_3$-$C_5$ halocycloalkoxy.

2. A compound of claim 1, wherein X and a halogen of the $C_2$-$C_8$ haloalkenyl are respectively selected from the group consisting of fluorine, chlorine, bromine and iodine.

3. A compound of claim 1, wherein $R_1$ is selected from the group consisting of methoxy, ethoxy, haloethyl, propoxy, halopropyl, butoxy, halobutyl, isobutoxy, pentoxy, halopentyl, isopentoxy, cyclopentyl, heptyl, heptoxy, haloheptyl, isoheptyl, isoheptoxy, cycloheptyl, octyl, octoxy, halooctyl, isooctyl, isooctoxy and cyclooctyl.

4. A compound of claim 1, wherein $R_1$ is selected from the group consisting of vinyl, vinyloxy, halovinyl, propenyl, propenoxy, halopropenyl, butenyl, butenoxy, halobutenyl, isobutenyl, isobutenoxy, haloisobutenyl, pentenyl, pentenoxy, halopentenyl, isopentenyl, isopentenoxy, haloisopentenyl, cyclopentenyl, hexenyl, hexenoxy, halohexenyl, cyclohexenyl, heptenyl, heptenoxy, haloheptenyl and cycloheptenyl.

5. A pharmaceutical composition, comprising: a therapeutically effective amount of a compound of formula (I):

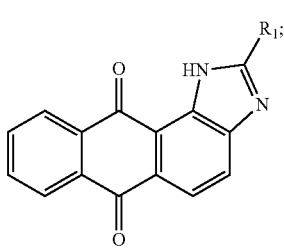

and at least an excipient or a carrier,
wherein $R_1$ is selected from the group consisting of:
i) amino, nitro, hydroxy and cyano;
ii) $(CH_2)_nX$, straight $C_6$-$C_{12}$ alkyl, $C_1$-$C_5$ alkyl $C_5$-$C_7$ alkyl, $C_1$-$C_{12}$ alkoxy, unsubstituted $C_3$-$C_{12}$ cycloalkyl, $C_1$-$C_5$ alkyl $C_3$-$C_{12}$ cycloalkyl, $C_3$-$C_4$ cycloalkoxy and $C_3$-$C_{12}$ cycloalkyl substituted with at least one substituent selected from the group consisting of straight or branched $C_1$-$C_{12}$ alkyl, amino, nitro, hydroxy, cyano, straight or branched $C_1$-$C_{12}$ haloalkyl, $C_{1-5}$ alkoxy, $C_1$-$C_5$ haloalkoxy, $C_3$-$C_5$ cycloalkoxy and $C_3$-$C_5$ halocycloalkoxy, wherein X is a halogen and n is 1, 2, 3, 4, 5, 6, 7, 8, 9, 10, 11 or 12;

iii) straight $C_2$-$C_8$ alkenyl, $C_1$-$C_3$ alkyl $C_2$-$C_5$ alkenyl, $C_2$-$C_8$ alkenyloxy, $C_2$-$C_8$ haloalkenyl, $C_3$-$C_8$ cycloalkenyl and $C_1$-$C_3$ alkyl $C_3$-$C_8$ cycloalkenyl; and iv) unsubstituted $C_5$ heterocyclyl, unsubstituted $C_7$-$C_{12}$ heterocyclyl and $C_5$-$C_{12}$ heterocyclyl substituted with at least one substituent selected from the group consisting of straight or branched $C_1$-$C_{12}$ alkyl, amino, nitro, hydroxy, cyano, straight or branched $C_1$-$C_{12}$ haloalkyl, $C_1$-$C_5$ alkoxy, $C_1$-$C_5$ haloalkoxy, $C_3$-$C_5$ cycloalkoxy and $C_3$-$C_5$ halocycloalkoxy.

6. A pharmaceutical composition of claim 5, wherein X and a halogen of the $C_2$-$C_8$ haloalkenyl are respectively selected from the group consisting of fluorine, chlorine, bromine and iodine.

7. A pharmaceutical composition of claim 5, wherein $R_1$ is selected from the group consisting of methoxy, halomethyl, ethoxy, haloethyl, propoxy, halopropyl, butoxy, halobutyl, isobutoxy, pentoxy, halopentyl, isopentoxy, cyclopentyl, heptyl, heptoxy, haloheptyl, isoheptyl, isoheptoxy, cycloheptyl, octyl, octoxy, halooctyl, isooctyl, isooctoxy and cyclooctyl.

8. A pharmaceutical composition of claim 5, wherein $R_1$ is selected from the group consisting of vinyl, vinyloxy, halovinyl, propenyl, propenoxy, halopropenyl, butenyl, butenoxy, halobutenyl, isobutenyl, isobutenoxy, haloisobutenyl, pentenyl, pentenoxy, halopentenyl, isopentenyl, isopentenoxy, haloisopentenyl, cyclopentenyl, hexenyl, hexenoxy, halohexenyl, cyclohexenyl, heptenyl, heptenoxy, haloheptenyl and cycloheptenyl.

9. A compound of formula (III):

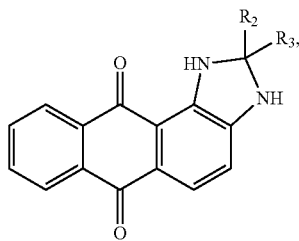

(III)

wherein $R_2$ and $R_3$ are each independently selected from the group consisting of:

straight $C_4$-$C_8$ alkyl, $C_1$-$C_3$ alkyl $C_2$-$C_8$ alkyl, straight $C_1$-$C_8$ haloalkyl, 2-methyl $C_3$-$C_8$ haloalkyl, $C_1$-$C_8$ alkoxy, $C_1$-$C_8$ haloalkoxy, $C_3$-$C_8$ cycloalkyl, $C_1$-$C_5$ alkyl $C_3$-$C_8$ cycloalkyl, $C_3$-$C_8$ cycloalkoxy, $C_3$-$C_8$ halocycloalkoxy, halophenyl, benzyl, benzyloxy, halobenzyl, phenethyl, phenethoxy and halophenethyl.

10. A compound of claim 9, wherein $R_2$ and $R_3$ are each independently selected from the group consisting of methyl, methoxy, halomethyl, ethoxy, haloethyl, propoxy, halopropyl, butyl, butoxy, halobutyl, isobutyl, isobutoxy, haloisobutyl, pentyl, pentoxy, halopentyl, isopentyl, isopentoxy, haloisopentyl, cyclopentyl, heptyl, heptoxy, haloheptyl, isoheptyl, isoheptoxy, haloisoheptyl, cycloheptyl, octyl, octoxy, halooctyl, isooctyl, isooctoxy, haloisooctyl, cyclooctyl and $C_1$-$C_3$ alkyl $C_3$-$C_8$ cycloalkyl.

11. A pharmaceutical composition, comprising: a therapeutically effective amount of a compound of formula (III):

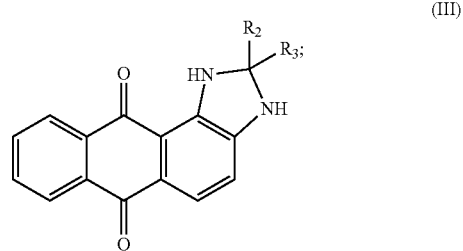

(III)

and at least an excipient or a carrier, wherein $R_2$ and $R_3$ are each independently selected from the group consisting of:

i) hydrogen; and ii) straight $C_2$-$C_8$ alkyl, $C_1$-$C_3$ alkyl $C_2$-$C_8$ alkyl, straight $C_1$-$C_8$ haloalkyl, 2-methyl $C_3$-$C_8$ haloalkyl, $C_1$-$C_8$ alkoxy, $C_1$-$C_8$ haloalkoxy, $C_3$-$C_8$ cycloalkyl, $C_1$-$C_5$ alkyl $C_3$-$C_8$ cycloalkyl, $C_3$-$C_8$ cycloalkoxy, $C_3$-$C_8$ halocycloalkoxy, halophenyl, benzyl, benzyloxy, halobenzyl, phenethyl, phenethoxy and halophenethyl.

12. A pharmaceutical composition of claim 11, wherein $R_2$ and $R_3$ are each independently selected from the group consisting of methyl, methoxy, halomethyl, ethyl, ethoxy, haloethyl, propyl, propoxy, halopropyl, butyl, butoxy, halobutyl, isobutyl, isobutoxy, haloisobutyl, pentyl, pentoxy, halopentyl, isopentyl, isopentoxy, haloisopentyl, cyclopentyl, heptyl, heptoxy, haloheptyl, isoheptyl, isoheptoxy, haloisoheptyl, cycloheptyl, octyl, octoxy, halooctyl, isooctyl, isooctoxy, haloisooctyl, cyclooctyl and $C_1$-$C_3$ alkyl $C_3$-$C_8$ cycloalkyl.

* * * * *

SEQUENCE LISTING

```
<160> NUMBER OF SEQ ID NOS: 3

<210> SEQ ID NO 1
<211> LENGTH: 6
<212> TYPE: RNA
<213> ORGANISM: Homo sapiens

<400> SEQUENCE: 1 aauccc                                                                    6

<210> SEQ ID NO 2
<211> LENGTH: 23
<212> TYPE: DNA
<213> ORGANISM: Homo sapiens

<400> SEQUENCE: 2
gggattggga ttgggattgg gtt                                                23

<210> SEQ ID NO 3
<211> LENGTH: 24
<212> TYPE: DNA
<213> ORGANISM: Homo sapiens

<400> SEQUENCE: 3
cccttaccct tacccttacc ctta                                               24
```